United States Patent [19]

Ranney

[11] Patent Number: 5,336,762

[45] Date of Patent: * Aug. 9, 1994

[54] POLYCHELATING AGENTS FOR IMAGE AND SPECTRAL ENHANCEMENT (AND SPECTRAL SHIFT)

[75] Inventor: David F. Ranney, Dallas, Tex.

[73] Assignee: Access Pharmaceuticals, Inc., Dallas, Tex.

[*] Notice: The portion of the term of this patent subsequent to Oct. 13, 2009 has been disclaimed.

[21] Appl. No.: 642,033

[22] Filed: Jan. 16, 1991

Related U.S. Application Data

[60] Division of Ser. No. 86,692, Aug. 7, 1987, abandoned, which is a continuation-in-part of Ser. No. 799,757, Nov. 18, 1985, abandoned.

[51] Int. Cl.$^5$ .................. A61K 49/00; C08B 37/02
[52] U.S. Cl. .......................... 534/16; 424/9;
536/102; 536/112; 536/121; 536/122; 556/45;
556/57; 556/138
[58] Field of Search ............... 424/9, 1.1; 536/51,
536/101, 121, 45, 57, 138; 530/391.3, 391.5;
128/653.4; 534/15, 16

[56] References Cited

U.S. PATENT DOCUMENTS

| | | | |
|---|---|---|---|
| 4,247,406 | 1/1981 | Widder et al. | 424/1.1 X |
| 4,370,476 | 1/1983 | Usher | 536/112 X |
| 4,385,046 | 5/1983 | Milbrath et al. | 424/1 |
| 4,423,158 | 12/1983 | Porath | 521/32 |
| 4,432,987 | 2/1984 | Widder et al. | 540/306 X |
| 4,452,773 | 6/1984 | Molday | 424/1.1 |
| 4,647,447 | 3/1987 | Gries et al. | 424/9 |
| 4,659,839 | 4/1987 | Nicolotti et al. | 424/1.1 X |
| 4,707,352 | 11/1987 | Stavianpoulos | 424/1.1 |
| 4,731,239 | 3/1988 | Gordon | 424/9 |
| 4,735,210 | 4/1988 | Goldenberg | 424/9 X |
| 4,735,796 | 4/1988 | Gordon | 424/9 |
| 4,770,183 | 9/1988 | Groman et al. | 424/9 X |
| 4,822,594 | 4/1989 | Gibby | 424/9 |
| 4,832,877 | 5/1989 | Bino et al. | 556/7 |
| 4,957,939 | 9/1990 | Gries et al. | 424/9 X |
| 4,963,344 | 10/1990 | Gries et al. | 424/9 |
| 4,985,233 | 1/1991 | Klaveness et al. | 424/9 |
| 4,986,980 | 1/1991 | Jacobsen | 424/9 |

FOREIGN PATENT DOCUMENTS

| | | |
|---|---|---|
| 0071564 | 2/1983 | European Pat. Off. . |
| 0124766A2 | 11/1984 | European Pat. Off. . |
| 0184899A1 | 6/1986 | European Pat. Off. . |
| 0186947 | 7/1986 | European Pat. Off. . |
| WO85/05554 | 12/1985 | PCT Int'l Appl. . |
| 2137612 | 10/1984 | United Kingdom . |

OTHER PUBLICATIONS

Lauffer, R. and Brady, T., "Preparation and Water Relaxation Properties of Proteins Labeled with Paramagnetic Metal Chelates," *Mag. Res. Imag.* 3:11-16 (1985).

Bino et al., "[$Cr_4S(O_2CCH_3)_8(H_2O)_4$]($BF_4$)$_2$·$H_2O$: Ferromagnetically Coupled $Cr_4S$ Cluster With Spin 6 Ground State", *Science,* 241:1479-1481 (1988).

Bulman et al., "Investigations Into Techniques for Removing Intracellular Plutonium-II, Complexing (List continued on next page.)

Primary Examiner—Richard D. Lovering
Assistant Examiner—John M. Covert
Attorney, Agent, or Firm—Arnold, White & Durkee

[57] ABSTRACT

The present invention includes an image-enhancing agent comprising a biodegradable, water-soluble polymer, synthetic or naturally derived and having repeating hydrophilic monomeric units with amino or hydroxyl groups. This agent also includes chelating agents comprising functional groups bound to an amino or hydroxyl group of the monomeric units. These chelating agents have a formation constant for divalent or trivalent metal cations of at least about $10^8$ at physiological temperature and pH. This image-enhancing agent is biodegradable to intermediary metabolites, excretable chelates, oligomers, monomers or combinations thereof of low toxicity. These image-enhancing agents may further comprise a paramagnetic metal ion for enhancement of the image arising from induced magnetic resonance signals. Images resulting from scanning of gamma particle emissions may be enhanced when the image-enhancing agent of the present invention comprises radioisotopic metal ions emitting gamma particles. The physical conversion of these image-enhancing agents into microspheres (or, less optimally, microaggregates) allows further internal directioning of the image-enhancing agents to organs with phagocytic capabilities. Dextran is a preferred polymer; DTPA and gadolinium are respectively preferred chelating agents and paramagnetic metal ions.

28 Claims, No Drawings

OTHER PUBLICATIONS

Agents Bound to Macromolecules," *Health Physics* 40:228–231 (1990).

Martell, A., "The Design and Synthesis of Chelating Agents," *Development of Iron Chelators for Clinical Use* pp. 67–104 (1981).

Dawson, et al., "Progress Toward the Synthesis of Polymerically Bound Chelating Agents for Iron(III) and the Development of a New Assay Method for Determining Iron Chelator Effectiveness," *Development of Iron Chelators for Clinical Use*, pp. 201–209 (1981).

Lauffer, et al., "Iron-EHPG as an Hepatobiliary Mr Contrast Agent: Initial Imaging and Biodistribution Studies," *Proc. Soc. Mag. Resonance in Med.*, pp. 883–884 (Aug. 1985).

Lauffer et al., "Preparation and Water Relaxation Properties of Proteins Labeled with Paramagnetic Metal Chelates," *Magnetic Resonance Imaging* 3:11–16 (1985).

Buonocore, et al., "Potential Organ Specific MRI Contrast Agents for Liver and Spleen: Gadolinium Labeled Liposomes," *Proc. Soc. Mag. Resonance in Med.*, pp. 838–839 (1985).

Widder et al., "Magnetically Responsive Microspheres as a Carrier by Site-Specific Delivery of Adriamycin," *Proc. Am. Assoc. Cancer Res.* 19:17, (Mar. 1978).

Blank et al., "Liposomal Encapsulated An-DTPA for Removing Intracellular YB," *Health Physics*, 39:913–920 (1980).

Erichsen et al., "Blockage of the Hepatic-Artery Blood Flow by Biodegradable Microspheres (Spherex ®) Combined with Local Hyperthermia in the Treatment of Experimental Liver Tumors in Rats," *J. Cancer Res. Clin. Oncol.* 109:38–41 (1985).

The 3M Bibliography on Tracer Microspheres (Feb. 1980).

Brasch et al., "Contrast-Enhanced NMR Imaging: Animal Studies using Gadolinium-DTPA Complex," *AJR* 142:625–630 (Mar. 1984).

Weinman et al., "Characteristics of Gadolinium-DTPA Complex: A Potential NMR Contrast Agent," *AJR* 142:619–624 (Mar. 1984).

Burnett et al., "Gadolinium Oxide: A Protoype Agent for Contrast Enhanced Imaging of the Liver and Spleen with Magnetic Resonance," *Magnetic Resonance Imaging*, 3:65–71 (1985).

Chen et al., "Paramagnetic Metalloporphyrins as Potential Contrast Agents in NMR Imaging," *FEBS Letters* 1274, vol. 168, No. 1:70–74 (1984).

Desreux, J., "Nuclear Magnetic Resonance Spectroscopy of Lanthanide Complexes with a Tetraacetic Tetraaza Macrocycle. Unusual Conformation Properties," *Inorg. Chem.* 19:1319–1324 (1980).

Kienle et al, "The Polyhydric Alcohol-Polybasic Acid Reaction. III. Further Studies of the Glycerol-Phthalic Anhydride Reaction," *J. Am. Chem. Soc.* 61:2258 (1939).

PCT International Search Report for International Appln. No. PCT/US/86/02479.

Biological Abstracts, vol. 78, 1984, Abstract 53968.

Runge, et al., "Work in Progress: Potential Oral and Intravenous Paramagnetic NMR Contrast Agents," *Radiology* 147:789–791, (Jun. 1983).

Dorland's Illustrated Medical Dictionary Twenty-Sixth Edition, p. 325.

POLYCHELATING AGENTS FOR IMAGE AND SPECTRAL ENHANCEMENT (AND SPECTRAL SHIFT)

This is a divisional of copending application Ser. No. 07/086,692 filed on Aug. 7, 1987 now abandoned, and international application PCT/US86/02479 filed on Nov. 18, 1986 and which designated the U.S. which is a continuation-in-part of pending U.S. patent application Ser. No. 799,757 filed Nov. 18, 1985, now abandoned and which is expressly incorporated by reference herein.

The present invention relates to image-enhancing agents, contrast agents or spectral shift agents to enhance tissue or organ images or nuclear spectra obtained from live animals with ultrasound imaging radioisotope scanning or NMR imaging or spectroscopy.

The imaging of internal structures and organs of live animals has been an important aspect of medicine since the advent of X-ray usage for this purpose. Among the techniques more recently developed for such imaging are those involving scanning for emission of particles from an internally located radioisotope. Such radioisotopes preferably emit gamma particles and are generally isotopes of metallic elements. One problem common to the diagnostic usage of such gamma particle-emitting radioisotopes concerns the localization of these materials at sites of particular interest rather than to have them randomly dispersed or rapidly excreted, by the kidney, for example. Another problem of such radioisotope mediated imaging concerns optimizing the circulating half-life of radioisotopes, for example, by preventing or accentuating their binding to serum proteins (e.g., albumin), or by prior conjugation (complexation) to polymeric carriers or receptor-binding substances.

A second class of internal body imaging which is undergoing a rapid growth in clinical use is ultrasound imaging. This is based on the detection of differences in the internal velocity (reflectivity) of directed, high-frequency sound waves. Differences in image brightness are produced at the interfaces between tissues with different native densities and ultrasound reflectivities. A present clinical problem is the difficulty of visualizing lesions in the stomach, small and large bowel, bladder, and cavities of the female reproductive tract, due to similarities of ultrasound velocity between these organs of interest and immediately adjacent tissues. Diagnostic introduction of a dense, nonradioactive metal element or ion at sufficient concentrations can confer the significant differences in ultrasound reflectivity which are required to visualize otherwise undetectable tumors and inflammatory lesions.

NMR intensity and relaxation images have been shown in recent years to provide a third important method of imaging internal structures and organs of live animals. Clinical magnetic resonance Imaging (MRI) is a rapidly growing, new form of brain and body imaging. Low-field (proton) MRI detects chemical parameters in the immediate environment around the protons of body tissues (predominantly water protons because of their relative abundance). Changes in these parameters occur very early in disease and are independent of physical densities detected by ionizing radiation. In the brain and central nervous system, MRI has allowed detection of tumors at an earlier clinical stage and with fewer imaging artifacts than is possible with computerized axial tomography (CAT) (Rungs et al., (1983) Am. J. Radiol V 141, p 1209). Under optimal conditions, image resolution is in the submillimeter size range.

Seven factors make it important to develop nontoxic MRI image-enhancing agents analogous to those available for CAT. 1. They increase the specificity of MRI diagnosis. 2. Smaller lesions can be identified earlier. 3. Image-enhancing agents enhance tumor masses differently than surrounding edema fluid or abscesses. This allows the extent and invasion of tumors to be defined more precisely. Lesions with infiltrative-type growth (e.g., certain metastatic carcinomas and glioblastomas) will require contrast agents for demarcation between tumor and edema fluid (Felix et al. (1985) Proc. Soc. Mag. Res. Med. V 2, p 831). 4. Image-enhancing agents improve the distinction between recurrent tumor and fibrous tissue resulting from surgery and radiation. 5. Image-enhancing agents can decrease the time required per scan and potentially decrease the number of scans required per procedure. This increases the volume of procedures and decreases their expense. 6. Body imaging has a significantly lower resolution (typically 0.5–1.0 cm) and sensitivity (decreased signal-to-noise ratio) than brain imaging (Wesbey et al. (1983) Radiology V 149, p 175). These differences result from the Greater inhomogeneity of the magnetic field; the larger radiofrequency coil; unequal phase-pulsing of deep versus shallow nuclei; and motion artefacts produced by respiration, cardiac systole, gastrointestinal peristalsis, and voluntary muscle movement; and 7. Advanced (polymeric and microsphere) forms of contrast agents (see below) appear to be required for the optimal acquisition and interpretation of blood-flow and tissue-perfusion images and related spectral (phase) information.

The discrete intensities of a two-dimensional, Fourrier-transformed image are described by the following general equation (for spin-echo pulse sequences):

$$\text{Intensity} = N(H) \cdot f(v) \cdot \exp(-TE/T2) \cdot (1 - \exp(TE - TR/T1)), \text{ where:}$$

$N(H)$ = number of protons in the discrete tissue volume (spin density);

$f(v)$ = a function of proton velocity and the fraction of protons which are moving (e.g., due to following blood);

$TE$ = time between the radio frequency (rf) pulse and the detection of signal (spin-echo);

$TR$ = the interval between repetition of the rf pulse.

$T1$ = the time interval associated with the rate of proton energy transfer to the surrounding chemical environment (spin-lattice relaxation);

$T2$ = the time interval associated with the rate of proton energy transfer, one to other (spin-spin relaxation).

The T1 and T2 times have reciprocal effects on image intensity. Intensity is increased by either shortening the T1 or lengthening the T2. Tissue contrast occurs naturally and is related to variations in the chemical environments around water protons (major contributor) and lipid protons (usually minor). Chemical agents have been used to enhance this natural contrast. The one most widely tested clinically is the paramagnetic metal ion, gadolinium ($Gd^{+3}$) (Rungs et al. (1983) Am. J. Radiol V 141, p 1209 and Weinman et al. (1984) Am. J. Radiol V 142, p 619). Although gadolinium shortens both the T1 and T2 times, at the lower doses used for clinical imaging, the T1 effect generally predominates and the image becomes brighter. Also, the rf pulse sequence can be programmed to accentuate T1 changes and diminish those due to T2 (Rungs et al. (1983) Am. J. Radiol V 141, p 1209). Hence, "T1-weighted" enhancement can be achieved by selecting the most favorable Gd dose and rf pulse sequence.

The shortening of proton relaxation times by Gd is mediated by dipole-dipole interactions between its unpaired electrons and adjacent water protons. The effectiveness of Gd's magnetic dipole drops off very rapidly as a function of its distance from these protons (as the sixth power of the radius) (Brown (1985) Mag. Res. Imag. V 3, p 3). Consequently, the only protons which are relaxed efficiently are those able to enter Gd's first or second coordination spheres during the interval between the rf pulse and signal detection. This ranges from $10^5$ to $10^6$ protons/second ((Brown (1985) Mag. Res. Imag. V 3, p 3). Still, because Gd has the largest number of unpaired electrons (seven) in its 4f orbital, it has the largest paramagnetic dipole (7.9 Bohr magnetons) and exhibits the greatest paramagnetic relaxivity of any element (Runge et al. (1983) Am. J. Radiol V 141, p 1209 and Weinman et al. (1984) Am. J. Radiol V 142, p 619). Hence, Gd has the highest potential of any element for enhancing images. However, the free form of Gd is quite toxic. This results in part, from precipitation at body pH (as the hydroxide). In order to increase solubility and decrease toxicity, Gd has been chemically chelated by small organic molecules. To date, the chelator most satisfactory from the standpoints of general utility, activity, and toxicity is diethylenetriamine pentaacetic acid (DTPA) (Runge et al. (1983) Am. J. Radiol V 141, p 1209 and Weinman et al. (1984) Am. J. Radiol V 142, p 619). The first formulation of this chelate to undergo extensive clinical testing was developed by Schering AG-Berlex Imaging according to a patent application filed in West Germany by Gries, Rosenberg and Weinmann (DE-0S 3129906 A 1 (1981). It consists of Gd-DTPA which is pH-neutralized and stabilized with the organic base, N-methyl-D-glucamine (meglumine). The Schering-Berlex agent is nearing completion of Phase III clinical testing at selected centers across the United States and abroad. The results of preliminary studies indicate that almost all human brain tumors undergo significant enhancement (Felix et al. (1985) Proc. Soc. Mag. Res. Med. V 2, p 831 and K. Maravilla, personal communication). These include metastatic carcinomas, meningiomas, gliomas, adenomas and neuromas. Renal tumors are also enhanced satisfactorily (Lanaido et al. (1985) Proc. Soc. Mag. Res. Med. V 2, p 877 and Brasch et al. (1983) Am. J. Radiol. V 141, p 1019). The Schering-Berlex formulation is projected to be available for general clinical use in 1987.

Despite its satisfactory relaxivity and toxicity, this formulation has four major disadvantages.

(1) Chelation of Gd markedly decreases its relaxivity (by $\frac{1}{2}$ an order of magnitude). This happens because chelators occupy almost all of Gd's inner coordination sites which coincide with the strongest portion of the paramagnetic dipole (Koenig (1985) Proc. Soc. Mag. Res. Med. V 2, p 833 and Geraldes et al. (1985) Proc. Soc. Mag. Res. Med. V 2, p 860).

(2) Gd-DTPA dimeglumine, like all small paramagnetic metal chelates, suffers a marked decrease in relaxivity at the higher radio frequencies used clinically for proton imaging (typically 15 MHz) (Geraldes et al. (1985) Proc. Soc. Mag. Res. Med. V 2, p 860).

(3) Due to its low molecular weight, Gd-DTPA dimeglumine is cleared very rapidly from the bloodstream ($\frac{1}{2}$ in 20 minutes) and also from tissue lesions (tumors) (Weinman et al. (1984) Am. J. Radiol V 142, p 619). This limits the imaging window (to ca. 30 to 45 minutes); limits the number of optimal images after each injection (to ca. 2); and increases the agent's required dose and relative toxicity.

(4) The biodistribution of Gd-DTPA is suboptimal for imaging of body (versus brain) tumors and infections. This is due to its small molecular size. Intravenously administered Gd-DTPA exchanges rapidly into the extracellular water of normal tissues, as well as concentrates in tumors and infections. This is facilitated by an absence in body organs, of the "blood-brain" vascular barrier which partly restricts the exchange of Gd-DTPA into the extracellular water of normal (versus diseased) brain. The result in body organs, is a reduced difference in the concentration of Gd-DTPA between normal and diseased regions of tissue, and hence, reduced image contrast between the normal and diseased regions of the organ. Also a disproportionate quantity (>90%) of Gd-DTPA is sequestered very rapidly in the kidneys (Weinman et al. (1984) Am. J. Radiol V 142, p 619). Of much greater interest to body MRI, are the abdominal sites involved in the early detection and staging of tumors (particularly the liver, and also the spleen, bone marrow, colon and pancreas).

Three approaches have been taken in attempts to overcome these disadvantages.

(1) Alternative, small chelating molecules have been tested. These make Gd more accessible to water protons but still chelate the metal with a sufficient affinity to potentially control its toxicity in vivo. The most effective of these chelators is DOTA, the polyazamacrocyclic ligand, 1,4,7,10-tetraazacyclododecane-N,N',N"-tetraacetic acid (Geraldes et al. (1985) Proc. Soc. Mag. Res. Med. V 2, p 860). Its relaxivity is approximately 2 times greater than that of Gd-DTPA over a wide range of Larmor frequencies. However, it is still less active than free Gd.

(2) Gd and Gd-chelates have been chemically conjugated to macromolecules, primarily the proteins, albumin (Bulman et al. (1981) Health Physics V 40, p 228 and Lauffer et al. (1985) Mag. Res. Imaging V 3, p 11), asialofetuin (Bulman et al. (1981) Health Physics V 40, p 228), and immunoglobulins (Lauffer et al. (1985) Mag. Res. Imaging V 3, p 11 and Brady et al. (1983) Soc. Mag. Res., 35 2nd Ann. Mtg., Works in Progress, San Francisco, Calif.). This increases the relaxivity of Gd by slowing its rate of molecular tumbling (rotational correlation time) (Lauffer et al. (1985) Mag. Res. Imaging V 3, p 11). This improves coupling of the energy-transfer process between protons and Gd (Geraldes et al. (1985) Proc. Soc. Mag. Res. Med. V 2, p 860, Lauffer et al. (1985) Mag. Res. Imaging V 3, p 11 and Brown et al. (1977) Biochemistry V 16, p 3883). Relaxivities are increased by multiples of 5 to 10 relative to Gd-DTPA (when compared as $R1=1/T1$ values at 1 millimolar concentrations of Gd) and by multiples of 2.5 to 5.0 (when compared as the molarities of Gd required to produce a specified decrease in the T1 relative to a control solution (physiologic saline).

The reasons for using the latter method of comparison are that 1) millimolar concentrations of Gd are never achieved in vivo—actual tissue concentrations achieved in the usual image enhancement are between 20 and 100 micromolar Gd; 2) the slopes of R1 graphs are frequently nonparallel for different enhancing agents; 3) the second method allows agents to De compared according to the more customary means of chemical activity ratio, in other words, as the concentration required to produce a specified percentage decrease in the T1 (or T2) relaxation time. Although R1 data are supplied below for the purpose of literature comparisons the second method is considered preferable and is the one used for internal comparisons of potency throughout the remainder of the application. The large drawback of conjugating DTPA to protein carriers for use in NMR image enhancement is that it has been difficult to stably conjugate more than 5 DTPA's (and hence Gd's) to each albumin molecule (Bulman et al. (1981) Health Physics V 40, p 228, Lauffer et al. (1985) Mag. Res. Imaging V 3, p 11 and Hnatowich et al. (1982) Int. J. Appl. Radiat. Isot. V 33, p 327 (1982).

Comparably low substitution ratios (normalized for molecular weight) have been reported for immunoglobulins (Lauffer et al. (1985) Mag. Res. Imaging V 3, p 11 and Brady et al. (1983) Soc. Mag. Res., 2nd Ann. Mtg., Works in Progress, San Francisco, CA) and fibrinogen (Layne et al. (1982) J. Nucl. Med. V 23, p 627). This results from the relative difficulty of forming amide bonds, the comparatively low number of exposed amino groups on typical proteins which are available for coupling, and the relatively rapid hydrolysis of DTPA anhydride coupling substrate which occurs in the aqueous solvents required to minimize protein denaturation during conjugation (Hnatowich et al. (1982) Int. J. Appl. Radiat. Isot. V 33, p 327 (1982) and Krejcarek et al. (1977) Biochem. Biophys. Res. Comm. V 77, p 581). The overall effect of these suboptimal conditions is that a very large dose of carrier material is required to achieve significant in vivo effects on MR images. At this high dose, the carrier produces an unacceptable acute expansion of the recipient's blood volume by an osmotic mechanism. Indeed, low substitution ratios have generally limited the use of such protein-chelator-metal complexes to the more sensitive (low-dose), radiopharmaceutical applications (Layne et al. (1982) J. Nucl. Med. V 23, p 627).

An attempt to overcome this low substitution ratio has been made by conjugating DTPA to the non-protein carrier, cellulose (Bulman et al. (1981) Health Physics V 40, p 228), however the chemical method employed results in continued suboptimal substitution of DTPA to carrier, the nonbiodegradability of cellulose and its water-soluble derivatives and the reported molecular aggregation which results from organic-solvent conjugation (in dimethylformamide) of CNBr-activated cellulose to the diaminohexyl spacer groups which link the carrier to DTPA, have rendered this class of carrier-conjugates unacceptable for intravenous administration at the doses required for MR image enhancement.

A very important consideration in the image enhancement of solid tumors and inflammatory lesions by polymeric contrast agents is that, in order for these agents to extravasate (exit) efficiently from the microcirculation into adjacent diseased tissues, they must be completely soluble—e.g., not be contaminated by inter molecular or supramolecular microaggregates. Optimal tumor access and localization requires that the molecular size of such agents generally be less than approximately 2,000,000 daltons (ca. 2 to 3 nanometers in molecular diameter), and preferably less than 500,000 daltons (ca. 0.5 to 1 nanometer in molecular diameter) (Jain (1985) Biotechnology Progress V 1, p 81). For this reason, with rare exceptions (see Example 6, below) the particulate and microaggregate classes of contrast agents (which comprise the liposomes, colloids, emulsions, particles, microspheres and microaggregates, as described below) do not concentrate efficiently in most solid tumors and inflammatory lesions. Instead, following intravenous administration, these supramolecular-sized agents: a) are first circulated in the bloodstream for relatively short intervals (25 minutes to 24 hours, depending on size), potentially allowing direct image enhancement of the blood pool (plasma compartment); and b) are subsequently cleared by specialized (phagocytic) cells of the reticuloendothelial tissues (liver, spleen and bone marrow), potentially allowing selective enhancement of these normal tissues, but producing indirect (negative) enhancement of lesions within these tissues (due to exclusion of the agents from the diseased regions). Additionally, following installation into the gastrointestinal tract and other body cavities, these particulate and microaggregate classes of agents can produce direct image enhancement of the fluids within these cavities, and thereby potentially delineate mass lesions which encroach upon the lumens and cavities. Both microspheres and microaggregates are supramolecular in size. The microaggregate class of agents is produced (intentionally or unintentionally) by either a) molecular cross-linking of individual polymer molecules or b) secondary aggregation of previously singlet (soluble) polymers, as induced by charge attraction or hydrophobic bonding mechanisms. It is distinguished from the microsphere class of agents by virtue of its smaller particle size, which ranges from approximately 2,000,000 daltons (ca. 2 to 3 nanometers in diameter) to 0.1 micrometers (=100 nanometers in diameter). It is important to note that microaggregates are cleared by reticuloendothelial phagocytes with significantly less efficiency and rapidity than are microspheres. In general, this property makes microaggregates a less preferred class of agents for visualizing the liver, spleen and bone marrow under the usual conditions of clinical imaging, for which prompt post-injection contrast enhancement is required.

(3) Gd-DTPA has been entrapped in liposomes (Buonocore et al. (1985) Proc. Soc. Mag. Res. Med. V 2, p 838) in order to selectively enhance images of the reticuloendothelial organs (liver, spleen and bone marrow) and potentially the lungs. Liver clearance is mediated by phagocytic (Kupffer) cells which spontaneously remove these small (0.05 to 0.1 um) particles from the bloodstream (Buonocore et al. (1985) Proc. Soc. Mag. Res. Med. V 2, p 838). (Particles larger than 3 to 5 um are selectively localized in the lungs due to embolic entrapment in lung capillaries.) A recent report indicates that the small-sized Gd-liposomes produce effective decreases in liver T1's (as determined spectroscopically without imaging) (Buonocore et al. (1985) Proc. Soc. Mag. Res. Med. V 2, p 838). Also, insoluble Gd-DTPA colloids have recently been reported to enhance MR images of rabbit livers under in vivo conditions (Wolf et al. (1984) Radiographics V 4, p 66). However, three major problems appear to limit the diagnostic utility of these devices. The multilamellar, lipid envelopes of liposomes appear to impede the free diffusion of water protons into the central, hydrophobic cores of these carriers, as assessed by the higher doses of Gd required for in vitro relaxivities equivalent to Gd-DTPA dimeglumine (Buonocore et al. (1985) Proc. Soc. Mag. Res. Med. V 2, p 838). This increases the relative toxicity of each Gd atom.

Even more importantly, these same lipid components cause the carriers to interact with cell membranes of the target organs in a way which leads to a marked prolongation of tissue retention (with clearance times of up to several months) (Graybill et al. (1982) J. Infect. Dis. V 145, p. 748 and Taylor et al. (1982) Am. Rev. Resp. Dis. V 125, p 610); and G. Kabala, personal communication). Two adverse consequences result. First, image enhancement does not return to baseline in a timely fashion. This precludes re-imaging at the short intervals (ca. 1 to 3-weeks) needed to assess acute disease progression and treatment effects. Second, significant quantities of the liposomally entrapped Gd-DTPA may be transferred directly into the membranes of host cells (Blank et al. (1980) Health Physics V 39, p 913; Chan et al. (1985) Proc. Soc. Mag. Res. Med. V 2, p 846). This can markedly increase the cellular retention and toxicity of such liposomal agents. The consequences for Gd toxicity have not yet been reported. Protein (albumin) microspheres with entrapped Gd and Gd chelates have been prepared and determined by the present applicant and others (Saini et al. (1985) Proc. Soc. Mag. Res. Med. V 2, p 896) to have only modest effects on T1 relaxivity in vitro. This is because most of the Gd as well as other entrapment materials (Widder et al. (1980) Cancer Res. V 40, p 3512) are initially sequestered in the interior of these spheres and are released very slowly as the spheres become hydrated (with $t_{\frac{1}{2}}$'s of hours) (Widder et al. (1980) Cancer Res. V 40, p 3512). This phenomenon has been found by the present applicant to markedly reduce the acute (30-to-90-minute) relaxivity of each Gd atom to approximately 1/10th that of Gd-DTPA dimeglumine. Hence, both the quantity of carrier material and the toxicity of Gd are both unnecessarily high.

Emulsions of insoluble, gadolinium oxide particles have been injected into experimental animals with significant image-enhancing effects on the liver (Burnett et al. (1985) Magnetic Res. Imaging V 3, p 65). However, these particles are considerably more toxic than any of the preceding materials and are inappropriate for human use. Because of the significant disadvantages of existing MR image contrast agents, the present applicant has formulated improved, second-generation prototype agents with reduced toxicity, increased selectivity of tumor and organ uptake, as well as a significant potential for enhancing blood flow images.

Many of the advantages shown for the present developments concerning NMR image-enhancing agents (also referred to herein as NMR contrast agents or MR (magnetic resonance) contrast agents) are also expandable to other areas. For example, high-field NMR surface-coil spectroscopy of $^1H^{13}C$, $^{19}F$, $^{23}Na$, and $^{31}P$ nuclei in spacially localized tissue volumes is gaining in importance and is starting to be applied experimentally to the noninvasive clinical monitoring of genetic and metabolic disorders; myocardial infarcts and metabolism; brain, liver and tumor metabolism; drug distribution and metabolism; blood flow and tissue perfusion measurements; and temperature monitoring in regional hyperthermia. Gadolinium and related agents can produce characteristic changes in the NMR spectrum of adjacent NMR-susceptible nuclei. These changes include: modulation of emission peak positions, widths, intensities, and relaxation rates (which affect intensity). Hence, perturbation of spectra by such chemical shift-relaxation agents can be used to localize and identify the source of NMR signals with respect to organ location, tissue compartment (intravascular versus extravascular), cell type within the tissue, and potentially, the specific metabolic pathways within cells which are altered by drugs and disease. Also in certain situations, ultrasound imaging or body scanning of radioisotopic emissions is particularly useful in achieving insight into internal structures. The radioisotopic emissions most frequently scanned are those of metallic radioisotopes emitting gamma particles, however, positron emission tomography is expaexperiencing increased clinicsl use. The molecular formulation and mode of administering these radioisotopic metals will have significant consequences on the internal localization and body half-life of these radioisotopes, potentially leading to increased diagnostic usage of these ultrasound images and emission scannings.

The present invention includes an image-enhancing or spectral-shift agent comprising a biodegradable, water-soluble polymer, synthetic or derived from natural sources and having repeating hydrophilic monomeric units with a high frequency of amino or hydroxyl groups. This agent also includes chelating agents comprising functional groups bound to an amino, quaternary ammonium or other reactive nitrogen group; hydroxyl; carboxy; sulfhydryl; sulfate or sulfonium group of the monomeric units. These chelating agents have a formation constant for divalent or trivalent metal cations of at least about $10^8$ (and typically $>10^{13}$) at physiological temperature and pH. The conjugation of chelating groups to the polymer (or to form the copolymer) is carried out under chemical conditions and in a solvent which yields a completely soluble (singlet) form of the carrier and avoids significant contamination by microaggregates. The molar ratio of chelating agent/monomeric unit is preferably between about 1/5 and about 1/25. The molar ratio of chelating agent/monomeric unit is preferably between about 1/5 and about 1/25. This image-enhancing agent is biodegradable to intermediary metabolites, rapidly excretable chelates, polymers, oligomers, monomers or combinations thereof, all of which have low toxicity and are cleared overwhelming by the renal route. The term "low toxicity" used herein means having little significant toxic effects at usable dosages of the image-enhancing agents.

These image-enhancing agents may further comprise a paramagnetic metal, transition element or rare-earth ion for enhancement of the images or spectra arising from induced magnetic resonance signals. As defined herein, the term "metal ions" refers to any of these materials as being capable of forming positively charged ions. The polymeric (or microsphere—see below) nature of these agents, is designed to produce a substantial increase in the NMR potency of each paramagnetic metal ion, compared to small metal chelates.

Images resulting from scanning of gamma or positron particle emissions may be enhanced when the image-enhancing agent of the present invention comprises a radioisotopic metal, transition element or rare-earth ion (or oxides of the preceding entities) emitting gamma or positron particles.

Images resulting from ultrasound scanning may be enhanced by modifying the native tissue reflectivity (velocity) of high frequency sound waves, when the image-enhancing agent of the present invention comprises one of the relatively dense, nonradioactive metals or metal ions.

The physical conversion of these soluble image-enhancing agents into microspheres (greater than or equal 100 nanometers in diameter). allows further internal targeting of the image-enhancing agents, either by oral administration to the gastrointestinal tract, or by intravenous administration to organs with phagocytic capabilities (principally liver, spleen and bone marrow).

The alternative conversion of these soluble image-enhancing agents into microaggregates (3 to 100 nanometers in diameter) also allows their internal targeting to phagocytic organs, but with substantially less efficiency and rapidity than occurs with microspheres.

Images of the internal structures of an animal may be obtained by a wide variety of means known to those skilled in the art. In one general field of imaging, the administration of metal, transition-element and rare-earth containing markers is utilized. These markers, because of the physical properties of their metal components, may be used to enhance the quality of images produced by numerous means.

Among the image-producing means where metallic transition element and rare-earth markers may be advantageously used are magnetic resonance (MR) imaging, ultrasound imaging and scanning of gamma and positron particle emissions. Foremost as a preferred embodiment of the present invention is the enhancement of images produced by nuclear magnetic resonance (NMR) imaging of whole animals or portions thereof. The terms magnetic resonance (MR) imaging and nuclear magnetic resonance (NMR) imaging are used herein as equivalent terms.

The present invention comprises novel ways to entrap metal- or paramagnetic metal-chelate complexes in biodegradable, hydrophilic polymeric microcarriers. First, the chelate is chemically conjugated in large numbers to hydrophilic polymers such as long-chain dextrans (1-6 linked, soluble, moderately branched polymers of glucose). These hydrophilic polymers are biodegradable and water-soluble. They are either synthetic or derived from eukaryotes, procaryotes, hybrid organisms, or plants and comprise repeating hydrophilic monomeric units having amino, hydroxyl or sulfate groups. They may be further deverizatized to contain carboxylic acid, sulfonium or sulfhydryl groups; or quaternary ammonium or other reactive nitrogen groups. The negatively charged, naturally occurring, repeating hydroxyl or sulfate groups may contribute to the stabilization of binding of positively charged Gd ions, over and above the stability of binding conferred by the covalently conjugated chelators.

The image-enhancing agents of the present invention comprise chelated or chelating agents having functional groups bound to hydroxyl, amino, quaternary ammonium (or other nitrogen functional group) , carboxy, sulfhydryl, sulfonium or sulfate group of the monomeric units of the polymer. These chelating agents are further defined as having formation (stability) constants for divalent or trivalent metal cations of at least about $10^8$ and typically greater than $10^{13}$ at mammalian physiological pH and temperatures.

The whole image-enhancing agents described above are characterized as being biodegradable by mammals to intermediary metabolites or excretable chelates, polymers, oligomers, monomers or combinations thereof, all of which have low toxicity.

Chelating agents having the properties described above have then the two basic properties of affinity for divalent or trivalent metals and also the ability to bond to one or more reactive groups as listed 2 paragraphs above, which themselves are bound to the polymer.

Particularly preferred chelating agents of the present invention include EDTA (ethylenediaminetetraacetic acid); DTPA (diethylenetriaminepentaacetic acid); TTHA (triethylenetetraaminehexa-acetic acid); and DOTA (1,4,7,10-tetrazacyclododecane-N,N',",N'''-tetraacetic acid).

A particularly preferred image-enhancing agent of the present invention comprises dextran polymer and DTPA chelating agent wherein the method of conjugation results in a polymer-chelate which is completely water soluble—e.g. avoids microaggregation—(see below). This particularly preferred agent, when in combination with gadolinium has been found to very effectively enhance internal (in vivo) images arising from induced magnetic resonance signals. Alternative elements (ions) for use in MRI could include those of atomic numbers 21 through 29 and 57 through 70, with particular emphasis on numbers 24–29 and 62–69.

The polymer of the image-enhancing agents described herein is preferably a polysaccharide or oligosaccharide and most preferably dextran. Polyamino substances, poly-L-lysine, for example, are usable but not generally preferred because of their net polymeric (closely spaced) positive charges at a physiological pH, although in conceivable circumstances this type of polymer could be desirable. In all cases, the polymers of the present invention should be biodegradable. This term "biodegradability", as used herein, indicates that internally available mammalian enzymes or conditions lead to the breakdown of the polymer, particularly to an excretable and non-toxic form. Thus non-biodegradable polysaccharides such as cellulose and its water-soluble derivatives are not preferred for the practice of the present invention. Biodegradability may indicate further that mammalian enzymes or conditions lead to cleavage of the chemical bond which attaches the metal chelator to the polymer or to the alternating monomeric units or the copolymer.

In size, the polymers of the present invention should have molecular weights of between 1,000 and 2,000,000 daltons. A more preferable size range for most uses is between about 40,000 daltons and about 75,000 daltons, this range representing a frequent optimum for the hybrid objectives of, amplifying the relaxivity of each Gd, allowing extravasation of an initially intravascular agent, and localization of this agent in tumors and inflammatory lesions, and of slightly-to-moderately delaying or otherwise modifying the renal excretion of these polymeric agents relative to lower molecular weight agents such as Gd:DTPA (dimeglumine).

The functional groups of the chelating agents are preferably bound to the monomeric units of the polymer by a covalent linkage, although in certain cases a strong noncovalent bond may be usable. The most preferable covalent bond of chelating agent to polymer is an ester linkage, due to its ease of formation, adequate stability for biological targeting, and optimal susceptibility to enzymatic cleavage for subsequent (post-imaging), clearance of the metal chelates from target cells and from the body.

The method used to conjugate the chelator to the carrier is of critical importance from the standpoint of agent solubility, and hence, biodistribution, performance, and acceptability of these soluble polymers in vivo. In order to obtain high substitution ratios of the chelator to carrier, and most importantly to avoid cross-linking the polymer singlets (prevent microaggregation), as well as to simplify chelator conjugation, minimize reagent expense, and facilitate subsequent biodegradation in vivo, conjugation of chelator groups when performed in the usual, side-chain configuration, is preferably carried out according to a one-step method which requires aqueous-phase coupling of the chelator's di-anhydride substrate, at a physiologic pH of less than 8.5, to carrier dextran of the desired molecular size. A carrier size of greater than approximately 10,000 to 20,000 daltons is preferred in order to provide the additional advantage of limiting the agents initial biodistribution almost exclusively to the blood vascular compartment (Grotte (1956) Acta Chirurgica Scandanavia V 211 (supplement), p 5). These features are required to: a) minimize the agent's access to the body's normal extracellular fluid, thereby providing maximal selectivity towards tumor imaging; b) allow maximal extravasation of the agent into tumors and inflammatory lesions (due to the capacity of completely soluble—e.g., nonaggregated—polymers of this size range to emigrate through the moderately enlarged "pores" which are present in tumor versus normal microvessels; and c) minimize clearance by reticuloendothelial phagocytes (which would reduce agent potency by removing it from the blood compartment, making it unavailable to tumors. These methodologic considerations are of utmost importance for maximizing agent usefulness, acceptability, and potency in vivo; optimizing renal clearance; and minimizing body toxicity.

Physical conversion of the soluble polymeric agent to microaggregates is possible but not preferred. However, it does occur inadvertently, and it can be achieved intentionally by either of the following chemical methods; a) by carrying out the chelator-carrier conjugation in any nonprotonating (organic) solvent. This facilitates the cross-linking (microaggregation) of adjacent polymer molecules because water hydrolysis of the chelator's second (unreacted) anhydride group cannot occur as rapidly as required after the first anhydride has reacted with a dextran molecules or b) by exposing the soluble (nonaggregated) form of the polymer-chelator-metal complex to pH's of approximately 8.5 or greater, which can produce microaggregation due to electrostatic (charge) effects.

A second preferable physical form of the image-enhancing agents of the present invention is one of microspheres. The preferable size range of these microspheres is between about 0.1 um and about 250 um. An NMR image-enhancing agent may be formed into microspheres, either before or after the addition of a paramagnetic metal ion such as that of gadolinium. The resultant microspheres, when administered at diameters less than 3 um to a mammal by intravenous injection have been found to be taken up by organs such as the liver, spleen and bone marrow. Thus the normal tissue components of these organs, for example, are rendered selectively preferentially able to yield improved images arising from induced magnetic resonance signals. Because of differential organ clearance, microspheres of sizes 0.1 to 3.0 um are preferable for image enhancement of liver, spleen and bone marrow; and microspheres of sizes 3 to 250 um are preferable for image enhancement of lung.

Another significant aspect of the present invention may involve the further rapid coupling of chelate-polymer image-enhancing agents themselves to proteins such as hormones, polyclonal or monoclonal antibodies or to a substance which secondarily binds either native or derivatized antibodies, (e.g., protein A, biotin or avidin). This coupling may involve, for example, sodium periodate oxidation of vicinal sugar hydroxyl Groups such as those of a polysaccharide and reduction of Schiff-bases by sodium borohydride to related, stable, covalent bonds with protein amino groups. The specific binding characteristics of antibodies, when combined with multiply chelatively bound metal ions may be used to produce specific localization of large numbers of paramagnetic or particle-emitting ions within internal targets of interest, thus amplifying greatly the signal-modulating effects of each specifically localized substance and also preserving or improving the antibody-binding specificity, affinity and avidity.

The image-enhancing agents of the present invention are also usable to enhance images being produced from the scanning of gamma and positron particle emissions and by ultrasound detectors. In this usage, most of the general principles of NMR image-enhancement—except agent dose—apply, the major difference being that now the chelated metal ion is respectively, a radioisotope which emits gamma particles, or one of the relatively nonradioisotopes which alters the velocity of transmitted and reflected ultrasound waves. Preferable radioisotopic metals include $^{51}$chromium, $^{68}$gallium, $^{111}$indium, $^{99}$technetium and its oxides. Useful ultrasound metals (ions) include those of atomic number 20 (calcium), 25 and 26 (manganese and iron, respectively), preferably 57–70 (the rare earth series), and optimally 64 (gadolinium).

A general object of the present invention comprises formulation and use of an image-enhancing agent, most particularly for images induced by magnetic resonance. This image-enhancing agent comprises a chelating agent bound to a water-soluble biodegradable polymer. The agent may be utilized in soluble form or as microspheres. In soluble form the image-enhancing agent, when administered to an animal, is primarily distributed in circulating blood, kidney and especially at sizes of about 20,000 to 500,000 MW, also has the capacity to exit the vascular compartment selectively in regions of tumors and inflammations and focus these tissue lesions.

In small microsphere form, the image-enhancing agent, upon administration by injection into animals, is preferentially cleared by and redistributed to liver, spleen and bone marrow. Upon oral administration, microspheres may be introduced into the gastrointestinal tract for image visualization thereof. Upon subsequent biodegradation in the small and large intestine, the preferred metal (e.g., gadolinium) will form insoluble oxides which are not absorbed internally, and are therefore nontoxic.

The acute enhancement of blood flow images, for example in the heart or cerebral vessels, may be accomplished with the soluble polymeric image-enhancing agent and is even more efficiently performed with the microsphere form.

A significant advantage of image enhancement with polymeric and microsphere chelators, in connection with the marginally toxic metals, particularly paramagnetic ones such as gadolinium, is a further reduction of necessary metal dose and decrease in toxicity over that which can be achieved by simple (low molecular weight) chelating agents alone.

The relatively rapid biodegradation and metal clearance times, and the resultant shorter re-imaging intervals are particular advantages involved with the present invention relative to other polymeric and particulate metal chelates and complexes.

The image-enhancing agents of the present invention, in soluble or microsphere form, are readily reconstituted for animal and patient administration. This reconstitution involves a simple vortex-type mixing, as compared to sonification in detergents used for protein-based microspheres.

The image-enhancing agents of the present invention are easily usable in any detection or imaging system involving administration of divalent or trivalent metallic marker ions. The appropriate metal need only be added to the polymer-chelate complex at pH's consistent with stable chelation binding (typically $\geq 3.0$ to 3.5) or the polymer-chelate complex be formulated as heat-stabilized or variously coated microspheres to protect against dechelation during passage through the more acidic environment of the stomach (typically pH=1.0–2.0).

The image or spectral enhancing agents of the present invention allow shorter image acquisition times for satisfactory internal resolutions. Shorter image acquisition times are generally adequate to produce satisfactory internal images because of the greater signal enhancement and image contrast produced per unit of chelated marker and total agent.

The potential for specific location of large numbers of marker metal ions by small numbers of monoclonal antibodies, nonpeptide and peptide hormones and receptor-binding substances tagged with one or more image-enhancing agents is contemplated as a major diagnostic advantage and future use.

Additionally, because of the high contrast, moderate prolongation of lesional residence times (soluble polymers) and liver, spleen and bone marrow residence times (microspheres) (of several hours versus minutes for small molecular forms) the use of the present image-enhancing agents allows an increased number of serial images to be obtained in the enhanced mode after a single administration of agent.

From a chemical point of view, some advantages of the present invention may be summarized as follows. When NMR image-enhancing agents comprise paramagnetic metals such as gadolinium ion, each gadolinium ion exhibits an increased relaxivity for adjacent magnetic nuclei (e.g. protons) and hence gives greater T1 signal enhancement. This increased relaxivity is related to an increased dipolar correlation time of Gd due to slower molecular rotation of polymeric Gd, the hydrophilic polymer (which becomes completely hydrated and allows rapid on-off binding (hence relaxation) of adjacent paramagnetic nuclei (protons)). Spacer groups are not required between the metal chelates and the polymeric carrier in order to obtain optimal paramagnetic relaxation potencies, however, they could be introduced if deemed advantageous for other purposes. When microspheres are used, the small microsphere size allows access of hydrated magnetic nuclei to virtually all of the chelated paramagnetic ions.

The chemically defined nature of preferred chelator-polymer combinations allows ready batch-to-batch uniformity for improved pharmaceutical formulations and a likely greater ease of FDA approval.

Many preferred components of the present invention, such as certain dextrans (40,000 and 70,000 MW forms), DTPA and Gd (as the DTPA chelate), for example have already separately achieved preliminary or final FDA approval.

For parenteral administration, these agents are preferably formulated as a sterile, physiologically balanced, aqueous solution (or suspension), whose pH for purposes of intravenous administration is either a) approximately 6.0 to 7.5 for biodistribution and localization of the soluble polymer, microspheres, or preformulated microaggregates; or b) 8.5 or greater for biodistribution and localization of microaggregates which were formed after conjugation of the chelator to soluble polymer, by electrostatic aggregation. Alternatively, these agents may be lyophilized and supplied in the dried from for reconstitution in physiologic solutions just prior to administration. For gastrointestinal administration (oral or rectal), or injection into body cavities (such as the bladder, uterus, Fallopian tubes, nasal sinuses or ventriculo-cerebrospinal system), these agents may be formulated as a physiological solution (or suspension) which contains additional substances to increase the viscosity or osmolality. For oral administration, the agents may be further formulated according to standard pharmaceutical methods, as uncoated or coated, micro- or mac-rotablets, in order to provide additional protection against the acidic pH of the stomach, and thereby avoid the release of chelated metal ions, which typically occurs at gastric pH's. Other additives, such as flavorings and colorings may be also incorporated according to standard pharmaceutical procedures.

For parenteral administration, the concentration of total active agent (polymer-metal chelate) will be between 0.1% and 30% (weight/volume), typically between 5% and 25%, and preferably 20%. Doses of the soluble polymeric and microsphere agents will vary depending on the paramagnetic metal and the route of administration. The following doses are given for intravenous administration For tumor image enhancement with the preferred embodiment, soluble Gd-DTPA-dextran 70, the dose will be between 0.01 and 0.075 millimoles of Gd per kilogram body weight, with optimal image enhancement occurring typically at or below 0.03 millimoles of Gd per kilogram. For liver, spleen and/or bone marrow enhancement with the preferred embodiment, microsphere Gd-DTPA-dextran 70, the dose will be between 0.008 and 0.05 millimoles of Gd per kilogram, with optimal image enhancement occurring typically at or below 0.01 millimoles per kilogram. For enhancement of the cardiovascular blood pool, the optimal dose of soluble Gd-DTPA-dextran 70 and microsphere Gd-DTPA-dextran 70 will occur, respectively, at or below 0.08 and 0.04 millimoles Gd per kilogram.

The following examples are presented to illustrate preferred embodiments of the present invention and their use in MR imaging. These examples are not intended to limit the scope of the present invention in any way unless otherwise so stated in the claims later appended hereto.

EXAMPLE 1

COMPARISON OF SPECIFIC ACTIVITIES AND R1 RELAXIVITIES OF IRON COMPLEXED TO DEXTRAN 70 AND LOW MOLECULAR WEIGHT IONIC IRON COMPOUNDS (FERRIC NITRATE AND FERRITIN-IRON)

$Fe^{+3}$ as the dextran-iron oxide (in which the iron is complexed loosely to the hydroxyl groups of dextran), was obtained as "Proferdex" (20% iron, w/w) (Fisons Pharmaceuticals) and tested, both before and after extensive dialysis (to remove loosely bound iron), for NMR T1-enhancing activity in vitro (using an IBM PC20 Minispectrometer, 20 MHz). This result was compared with those of $Fe^{+3}$ in the forms of ferric nitrate $(Fe(NO_3)_3.9H_2O$, obtained from Sigma Chemicals, St. Louis, Mo.) and iron-ferritin (obtained as apoferritin saturated with iron at 8.5% (w/w) (Polysciences, Inc.) in which $Fe^{+3}$ is entrapped inside the core cavity of the apoprotein at up to a 4,500:1 molar ratio to the protein, but in which the rotational correlation time of the ionic iron is not prolonged by virtue of direct conjugation to the protein. Following Table 1 describes many of the above results.

TABLE 1

| Compound | $Fe^{+3}$ concentration (ug/ml) producing a 50% decrease in water T1 | R1 relaxivity) (1/mmol × sec) |
|---|---|---|
| Dextran-Fe | 19 | 0.817 |
| Ferric nitrate | 42 | 1.476 |
| Fe-ferritin | 100 | 0.541 |

As assessed by the more accurate method (of $Fe^{+3}$ concentration producing a 50% decrease in the water proton T1 time), the loose conjugation of iron to macromolecular dextrans increased the specific paramagnetic activity of $Fe+3$ by a multiple of 2.21 relative to ferric nitrate (42/19 ug/ml)—lower Fe concentrations indicate a higher $^1H$ relaxivity per Fe atom. This increased T1-enhancing potency dextran-iron results from the slower rotational correlation time of iron following complexation to its larger, dextran carrier. Ferritin-Fe was less potent than ferric nitrate (50% activity multiple=0.42, corresponding to 42/100 ug/ml). This reduced potency results from partial sequestration of ionic iron in the core cavity of the apoferritin protein, which decreases the on-off rate of exchange of external water protons during the T1 relaxation interval. This potency decrease is observed even under conditions of a very minimal diffusional barrier imposed by the monomolecular coat of the entrapment protein. It corroborates the even larger decreases of relaxation potency which were reported and observed above, for paramagnetic metals entrapped within liposomes and stabilized albumin microspheres.

Whereas the significant enhancement of potency observed for dextran iron ("Proferdex") together with its macromolecular nature, suggested that it might be a suitable prototype T1-contrast agent for intravenous administration and restricted biodistribution (initially within the blood vascular compartment), extensive clinical trials (for treatment of iron deficienty anemias) had indicated that its intravenous (versus intramuscular) administration was followed frequently by systemic hypotension (Physicians Desk Reference (1986) p 1228). This was true especially if the agent was administered over an interval of several minutes, as would be required for MR image enhancement. This in vivo toxicity was thought to result from rapid release of the weakly complexed-iron (oxide). To elucidate this, dextran-iron was extensively dialyzed and the NMR T1 activity ratios of the entire molecules were compared by the 50% concentration method (above). By this method, only approximately 17.7% of the pre-dialysis iron remained complexed to the dextran carrier. This both explains the in vivo toxicity and indicates why dextran-iron (and by inference, other dextran-metal) oxide complexes are unlikely to represent preferred embodiments of the present invention. From these data, it was apparent that the preferred embodiment(s) for intravenous use would be more likely to comprise dextran carriers with covalently conjugated chelating groups which had stability constants for metal chelation which were significantly higher than those of dextran-iron oxide complexation (see following examples). However, dextran-iron could be of significant use for gastrointestinal and other parenteral applications in which iron release from the carrier was less critical.

EXAMPLE 2

PREPARATION OF DTPA-DEXTRAN

A. Conjugation In Aqueous Solvent

1. Preparation and Maintenance of Completely Soluble (Nonaggregated) Polymer Conjugates The cyclic dianhydride of DTPA, prepared by the method of Eckelman et al. (J. Pharm. Sci. V 64, pp 704–706 (1975)), was obtained in a highly pure form from Calbiochem-Behring Corp. 6.0 g of the cyclic dianhydride was added stepwise to 1.72 g of Dextran T70 (average MW 70,000 daltons, Pharmacia Chemicals) in a reaction solvent comprising HEPES buffer 115 mg/100 cc distilled water, pH 7.0 to 8.0 (maximally). The reaction was carried out with vigorous stirring at ambient temperatures for a 1 hr period with readjustment to pH 7.0 to 8.0 using NaOH, after each segmental addition of DTPA dianhydride. The dextran-DTPA product was separated from unconjugated DTPA by dialysis against 200 volumes of distilled water at pH 5.5. As assessed by molecular filtration, 97.8% of the dextran-DTPA product had a molecular weight of less than 100,000 daltons and only 1.6% had a molecular weight greater than 300,000 daltons. The dilute solution of dialyzed dextran-DTPA was concentrated to between 5% and 20% (w/v) by one of three methods: a) forced, filtered-air evaporation at room temperature (preferred); D; retention over a nitrogen pressurized, 10,000 MW cutoff filter (Amicon Corporation); or c) lyophilization and reconstitution in physiologic solutions. None of these methods produced a significant increase in the average molecular weight, as assessed by molecular filtration (above). This indicated that no significant inter molecular aggregation was induced by any of the three methods of concentration. In the first two methods (a and b, above), concentrated salts and buffers were added as needed, to render the final preparations physiologically acceptable for subsequent injection. In all cases, care was taken to maintain the pH at or below 8.0 (generally between 6.5 and 7.0), in order to prevent post-conjugation aggregation of the dextran-DTPA. (See below for intentional preparation of microaggregates from this soluble polymer.)

Gadolinium in the form of $GdCl_3$. $7.05H_2O$ (Alfa Laboratories, 2.1 g in 10 cc distilled water was added to 1.38 g of the concentrated dextran-DTPA conjugate in distilled water adjusted to pH 5.5 with NaOH. Unbound gadolinium was removed from the dextran-DTPA gadolinium complex by molecular filtration through a 10,000 MW cutoff filter. Free gadolinium was monitored by standard complexometric titrations using xylenol orange (Lyle et al. (1963) Talanta V 10, p 1177) and minimized for each preparation. Alternatively and preferred, the binding capacity of polymer was determined in advance and the quantity of Gd adjusted to be exactly stoichiometric, leaving neither free Gd nor free polymeric DTPA. This standard complexometric titration was also used to quantify total gadolinium of each preparation after oxidative acid hydrolysis of the organic matrix followed by neutralization of the released Gd. As recently prepared, one of every 12.2 sugar residues is conjugated to an active DTPA ligand, for a total of 32 Gd-binding ligands per 389 Glucose units. (It is anticipated that significantly higher derivatization ratios can be achieved without producing significant carrier cross-linking, by increasing the quantity of DTPA anhydride and maintaining more continuous control over the reaction pH with a pH stat.) The in vitro T1 relaxivity, R1, in physiologic saline is greater than $100/(mM \times sec)$ (IBM PC20 Minispectrometer, IBM Instruments). (By comparison, the R1 of $GdC1_3$ was $3.03/(mM \times sec)$. The osmolality of soluble Gd-DTPA-dextran T70 is at or below 3590 mOsm/kg product, as determined by the vapor pressure method (Wescor Model 5100B osmometer, Wescor Instruments). As a final quality-control check, the concentrated product, Gd-DTPA-dextran, was tested in an ionized calcium analyzer (Orion Biomedical Instruments) to assure that it had negligible calcium-binding capacity. This was done both as an additional check on the stoichiometry of Gd binding, and as a security measure to exclude any possibility of an acute decrease in serum calcium following intravenous injection (thereby avoiding cardiovascular complications and tetany).

Two other soluble DTPA-dextran derivatives of differing molecular weights were synthesized from starting dextrans of 10,000 MW (Dextran T10, Pharmacia Chemicals) and 40,000 MW (Dextran T40, Pharmacia Chemicals). These reactions were carried out in a fashion analogous to that just described, and the resulting conjugates were allowed to chelate Gd at stoichiometric quantities (determined by Gd+EDTA comlexiometric titration against xylenol orange), to form a) soluble Gd-DTPA-dextran T10 (MW=11,000; $R1=4.24/(mM \times sec)$); and b) Gd-DTPA-dextran T40 (MW=43,000).

2. Preparation of Microaggregates From the Soluble Polymer Conjugate

If desired, microaggregates (ranging from 3 to 100 nanometers in diameter) are produced directly from the soluble Gd-DTPA-dextran T70 polymer by adding NaOH to the product (at a concentration of at least 8% (w/v) in 0.02M phosphate buffer+0.15M NaCl) until the final pH is 8.2 or greater (preferably 8.5–9.0) and incubating the product for 16–48 hours at either room temperature or 4° C. Microaggregates form based on ionic charge effects, and these are stable from the standpoint of biodistribution to reticuloendothelial organs following intravenous administration (see Example 3).

B. Conjugation in Nonaqueous Solvent

This was carried out as above, except by suspending the initial reactants in N,N-dimethylformamide (preferred due to favorable temperature stability). A second solvent expected to allow comparable conjugation, is N,N-diethylacetamide; this may have a biological advantage comprising improved susceptibility of its two-carbon fragments to metabolism, and hence, reduced toxicity in vivo if trace quantities of organic solvent remained with the DTPA-dextran following dialysis. Because neither of the substrates (dextran nor DTPA anhydride) are fully soluble in N,N-dimethylformamide the kinetics of conjugation are quite slow (ca. 12 to 16 hours). Consequently, for the present reaction, 44 mg of highly pure bis-cyclic DTPA anhydride (Calbiochem-Behring Corp.) was added to 20 mg of Dextran T70 (average MW=70,000 daltons, Pharmacia Chemicals) suspended in 1.5 cc of dry N,N-dimethulformamide (Baker Chemicals) and the conjugation was accelerated by ultrasonification+vigorous stirring of the reaction mixture, either with or without cooling at 4° C. (both temperatures gave equivalent results). Under these conditions, DTPA conjugation proceeded rapidly and plateaued at 15 to 30 minutes. At this point, NaOH was added either a) in the form of powdered pellets at the completion of conjugation, just prior to hydrolyzing any excess unreacted DTPA dianhydride with a 2-fold excess of water (with vigorous stirring and sonication); or b) in the form of an aqueous solution, at the same time as hydrolysis of any excess unreacted DTPA dianhydride (both methods gave equivalent results). In attempts to minimize microaggregation due to pH, the quantity of NaOH was carefully adjusted to give a pH of 6.0 upon formation of the aqueous mixture. This nonaqueous method resulted in a 1.7 fold increase in complexing ratios of Gd to dextran T70 and dreased the DTPA dianhydride required by a factor of 1.8. As recently prepared in N,N-dimethylformamide, one of every 7.2 sugar residues is conjugated to an active DTPA ligand, for a total of 54 Gd-binding ligands per 389 glucose units. The resulting product has an R1 in physiologic saline of greater than $50/(mM \times sec)$. As assessed a) in vitro by microscopy and light scattering, and b) in vivo by biodistribution patterns (see below) the physical form of this organic-phase, DTPA-dextran conjugate was moderately to heavily predominantly microaggregated, with sizes ranging up to 0.1 to 0.2 micrometers in diameter.

An analogous, organic-phase synthesis was carried out by dissolving separately, the identical quantities as above of DTPA anhydride and dextran T70 in dimethylsulfoxide, mixing these together after maximal solution of the individual reagents had occurred, stirring the mixture for 8 to 18 hours at either 4° C. or 22° C. (both methods produced equivalent results, and hydrating the conjugates slowly (while stirring) with distilled water, with maintenance of pH at 7.0. Both methods produced conjugates whose physical form was moderately to heavily microaggregated, with sizes ranging up to 0.1 to 0.2 micrometers in diameter (assessed in vitro as described just above).

Compared to the preceding, aqueous-phase method, the slight advantages in substrate savings and derivatization ratios observed with this organic-solvent synthesis, are markedly offset by: a) the intermolecular cross-linking (covalent microaggregation) which occurs in (and is typical of) organic-phase conjugation (due to the very slow rate of second-group anhydride hydrolysis in nonprotonating solvents); and b) the reduced Gd relaxivity which apparently results from microaggregate-induced impedance of water proton exchange rates (see Example 4, table). This in turn, leads to marked disadvantages in the product's biodistribution, clearance rates, and tumor access following intravenous administration (see Example 3). Hence, aqueous- rather than organic-phase conjugations are the preferred methods for synthesizing polymeric intravascular contrast agents because organic-phase synthesis does not allow the formulation of completely soluble (noncross-linked) products. This feature is imperative for medical utility and regulatory acceptance.

C. General Features of DTPA-dextrans

Dextran-DTPA image-enhancing agents particularly with entrained gadolinium, were produced under a variety of conditions and with different dextrans in various batches. Each batch was lyophilized and, when stored at room temperature, found to be stable at 22° C. in excess of 1 year. Physiologic solutions of these agents were equally stable and gave no release of free Gd after 1 year at 4° C. Particular batches of dextran-DTPA image-enhancing agents were prepared having molecular weights of 10,000, 40,000 and 70,000 daltons although the method is usable for a size range of at least from 1,000 daltons to 2,000,000 daltons. The high derivatization ratio, which was observed for both aqueous and nonaqueous conjugations results from the increased ease of forming ester bonds relative to the amide bonds formed in conjugations to primary amines of proteins (see Background). Whereas ester bonds are sufficiently stable to allow initial targeting and tissue and cellular uptake which parallels that of the carrier molecule, these bonds are also more rapidly biodegraded in host cells add serum than are peptide bonds. This decreases toxicity by allowing faster cleavage of Gd-DTPA from the localized carrier, and hence, faster release from these sites of initial localization (entrapment) and more rapid and complete clearance of Gd-DTPA from the body by renal excretion (see Example 3). The increased rotational correlation time of the dextran macromolecule and its hydrophilic nature (which allows rapid on-off binding of water protons) amplify the paramagnetic efficiency (specific activity) of each Gd by multiples of 4.5 for the aqueous conjugate (soluble) and 2.2 for the nonaqueous conjugate (microaggregates) (see Example 4, Table). The net negative charge of hydroxyl Groups on the glucose residues (which are slightly ionized at physiologic pH) contributes to stabilization of $Gd^{+3}$ binding by electrostatic effects and hence increases the Gd stability constant to significantly above $10^{17}$. The combination of these properties cause the dose, in vivo bioexchange and toxicity of Gd to be substantially decreased. The high derivatization ratio (Gd-DTPA per dextran) also minimizes the amount of carrier material required for MR image enhancement in vivo. This reduces the total osmolality to levels which allow acute intravenous injection of MRI doses without producing unacceptable acute plasma volume expansion.

EXAMPLE 3

IN VIVO PHARMACOKINETICS AND BIODISTRIBUTION OF THE IMAGE-ENHANCING AGENTS

A. Soluble Agents

The soluble, 78,000 MW dextran-DTPA gadolinium chelates described in Example 1 (aqueous solvent method) have been injected directly into mice and rats. At the usual doses of 25 to 250 mg/kg, in rats, the chelated Gd has a blood clearance whose two major components have $t_{\frac{1}{2}}$'s of about 50 and 180 minutes, as assessed by radioisotopic 153Gd. This provides up to a3-fold increase in the MR imaging window compared to Gd-DTPA. The flexibility exists for coupling DTPA to biocompatible carbohydrate carriers of various molecular weights, ranging from 1,000 to 2,000,000 daltons. By using shorter chain lengths than 70,000 daltons (e.g. 1,500 to 40,000 daltons) clearance times could be shortened towards those of Gd-DTPA. This may also increase slightly the propensity of the contrast material to extravasate into tumors and inflammatory lesions. Alternative mono-, di-, oligo- and polysaccharides potentially include alpha, beta and gamma cyclodextrins, poly-cyclodextrins, glucose, glycogen, maltose, starch (and its derivatives, e.g., hydroxyethyl, carboxymethyl-, and aminoethyl-) blood-group oligosaccharides and their derivative amines, mucopolysaccharides and their oligomers, heparins, heparan, heparan-$SO_4$, chondroitin-$SO_4$, dermatan-$SO_4$, and related, natural and synthetic, water-soluble polycarbohydrates and their derivatives.

In mice, the blood clearance of the Gd in 153Gd-DTPA-dextran 70 occurs in $\frac{1}{2}$ to $\frac{1}{3}$ the ($t_{\frac{1}{2}}$) time observed in rats (above). Whereas clearance in rats is more predictive of that in humans, this accelerated clearance in mice has important implications for several of the subsequent examples involving in vivo potencies (in both the T1-relaxation and MR imaging modes), as follows. First, comparison of these NMR changes at a fixed time interval (e.g. 30 minutes post-injection) will make the soluble polymer appear to be more potent (for tumor imaging) in rats than in mice, whereas, if compared at times of equal blood levels, these two species of animal give equal results. Second, when the soluble polymer is compared with its microsphere formulation (made from the same soluble polymer) at e.g., a 30-minute post-injection interval, the microsphere formulation will appear to be considerably more potent (at enhancing liver) than is the soluble polymer (at enhancing tumors). This is because microsphere clearance from the liver occurs an order of magnitude more slowly (see below) than does soluble polymer clearance from a typical tumor. However, when monitored at appropriately shorter post-injection intervals (20 minutes in mice; 30–45 minutes in rats) the soluble polymer is actually very similar in potency to microspheres.

B. Microsphere Agents

In both rats and mice, the $t_{\frac{1}{2}}$ for blood clearance of the Gd in Gd-DTPA-dextran microspheres (0.1 to 0.5 micrometers in diameter) is ca. 15–20 minutes (as assessed by NMR T1 changes in the freshly excised organs). In rats, ca. 50% of this microsphere Gd is cleared within ca. 2 hours by the kidneys (same method). Initial studies (using both radioisotopic 153Gd and NMR T1 methods) indicate that the residual fraction of microsphere Gd which remains entrapped in the liver beyond 2 hours, clears with a $t_{\frac{1}{2}}$ of 5–6 days. This slower clearance occurs by both the gastrointestinal (major) and renal (minor) routes and is comparable in rate to that for the liver clearance of native dextran 70.

C. Microaggregated Agents

In mice, the blood clearance of the Gd in Gd-DTPA-dextran microaggregates (3–100 nanometers in diameter) ranged from 60–240 minutes depending of their size ($t_{\frac{1}{2}}$'s increasing with smaller size—153Gd method). Biodistributions also varied depending on size, however, typically 40% to 75% of the agent was cleared by the liver. Maximal liver levels occurred at 24 hours post injection. Subsequent liver clearance occurred with a $t_{\frac{1}{2}}$ of 5–6 days (same method).

Comparative Biodistributions of Soluble and Microaggregated Gd-DTPA-dextrans

The following table illustrates typical biodistribution results obtained at 33 minutes post-injection of $^{153}$Gd-DTPA-dextran T70 in tracer doses, as the soluble polymer and microaggregates, into Swiss nude mice bearing human (BRO) melanoma tumors.

| Organ | Organ concentration of Gd (uM) | |
|---|---|---|
| | Soluble Agent | Microaggregated Agent |
| Liver | 3.3 | 142.0* |
| Tumor (maximal) | 6.8 | 3.8 |
| Kidney | 18.7 | 16.2 |

*Liver sequestration of these microaggregates continues to increase over time and peaks at ca. 24 hours at 150% of this 33 min value. (This delayed increase is not observed for the soluble agent.)

For the microaggregated agent, tumor concentrations were reduced absolutely due to: a) strong competitive uptake by the liver, and b) the inaccessibility of supramolecular aggregates to tumors because of the smaller size of tumor capillary "pores".

EXAMPLE 4

PRODUCTION AND USE OF MICROSPHERES

The soluble polymer of Example 2 has also been reformulated as very small (0.1–0.5 um) hydrophilic microspheres, by a modification of the method reported by the Applicant in a recent issue of Science (V 227, p 182 (1985)). In summary, this method involved first the emulsification of the dextran-DTPA-Gd complex in an oil such as cottonseed oil. The emulsified complex was then sonicated to produce smaller microspheres. The oil was extracted with a volatile organic solvent (ether or hexanes) and the microspheres were lyophilized. In contrast to the liposomes and colloids discussed earlier herein, these new, very small hydrophilic microspheres allow almost complete access and rapid exchange of water protons to all the Gd throughout the sphere matrix. The R1 of microspheres in physiologic saline is greater than 90/(mM×sec). Hence, microsphere-Gd and polymer-Gd have almost identical T1 activities in vitro. This is consistent with the reported finding that increments in Gd relaxivity, which are produced by macromolecular coupling, plateau at macromolecular weights $\geq$65,000 daltons (Lauffer et al. (1985) Mag. Res. Imaging V 3, p 11). Hence, the slower rotation of microspheres relative to the soluble polymer, is not expected to give any further improvement in the relaxivity of microsphere-Gd over soluble macromolecular Gd (except potentially under flow conditions—see Example 8, below).

On intravenous injection, the microspheres are cleared (captured initially) spontaneously by the liver, spleen and bone marrow of mice and rats (at a t½ of approximately 15 minutes). Here, they undergo controlled dissolution to the soluble polymer at a t½ of 30 minutes. This selectively enhances NMR images of the preceding organs. Optimal T1 decreases have been obtained in the livers of mice using lower injected doses of Gd (0.01 to 0.02 mmoles/kg) than are normally used for standard contrast enhancement in clinical imaging (Gd-DTPA, 0.10 to 0.30 mmoles/kg). The latter agent produces minimal changes in liver T1's at the usual 30-minute imaging interval.

In rat studies, enhancement of liver images is achieved with microsphere doses 10 to 27 times lower than those required for Gd-DTPA. This significant dose advantage is produced by the combined effects of four design features: the increased rotational correlation time of microsphere-Gd, the improved permeation of water protons into the hydrophilic matrix and rapid on-off binding to (or near) Gd, the extremely small diameters of the microspheres, and the selective uptake of microspheres by target organs. As a result, these microspheres are effective in vivo at the lowest doses of any formulation reported (down to 0.007 mmoles/kg).

The following table describes many of the above described results.

CONCENTRATIONS OF TOTAL MATERIAL AND GADOLINIUM REQUIRED TO PRODUCE A 50% DECREASE IN THE T1 OF WATER PROTONS (IN VITRO) (IBM PC 20 MINISPECTROMETER, 20 MHz)

| Sample Material | Material Concentration (ug/ml) | Gadolinium Concentration (m/10$^{-5}$) | Gd specific activity ratio* |
|---|---|---|---|
| Soluble Gd-DTPA dimeglumine (Schering) | 90 | 9.59 | ** |
| Microsphere-entrapped but unconjugated Gd-DTPA (dimeglumine) | 65 | 4.22 | 2.3 |
| Soluble Dextran DTPA-Gd polymer (1 DTPA/22 glucose) (mw = 78,000 daltons) | 270 | 2.13 | 4.51 |
| Soluble Dextran DTPA-Gd polymer (1 DTPA/18 glucose) (MW = 11,000 daltons) | 280 | 7.14 | |
| Microspheres formulated from the 78,000 dalton Dextran-DTPA-Gd polymer | 300 | 2.36 | 0.90 |
| Microaggregates of Dextran-DTPA-Gd synthesized in DMF organic solvent (1 DPTA/7 glucose) | 80 | 4.35 | |

*Lower gadolinium concentrations indicate a higher $^1$H relaxivity per Gd atom. A higher specific activity ratio for T1 corresponds to an increase in the MR signal intensity achieved per gadolinium atom (and an increased image intensity obtained in vivo).
**These lines indicate the relationships producing the ratio.

EXAMPLE 5

IN VIVO NMR ENHANCEMENT OF NORMAL TISSUES: LIVER, SPLEEN AND BONE MARROW

Sprague-Dawley rats were imaged using a 0.35-Tesla, Diasonics clinical MR imaging system and a 30-cm rf coil. Three clinically relevant pulse sequences were used: 1) spin-echo with a TR of 0.5 seconds (for T1-weighted images), 2) inversion-recovery (IR) (for T1-weighted images), and 3) spin-echo with a TR of 2.0 seconds (for T2-weighted images). Diasonics software was used to calculate the area-averaged tissue intensities before and after injection of contrast agents. Dual pulse sequences (spin-echo, with TR's of 0.5 and 1.5 seconds or 1.0 and 2.0 seconds) were also used to calculate the in vivo T1 relaxation times. At the conclusion of imaging, the liver, spleen and kidneys were excised and their T1 (IR) and T2 (Carr-Purcell-Meiboom-Gill) relaxation times were determined at 37° C., using an IBM PC20 Minispectrometer. For these in vitro experiments, uninjected rats were used in place of preinjection controls.

Two contrast materials were compared at equivalent in vitro doses: 1) Gd:DTPA dimeglumine (0.3 mmoles/kg; Schering AG), and 2) the 0.1–0.5 um hydrophilic Gd:DTPA-dextran microspheres prepared by the Applicant from No. 2 (0.009 mmoles/kG); with an in vitro potency 4.1 times that of Gd:DTPA dimeglumine). Post-contrast images were obtained serially beginning immediately after the i.v. injection of contrast agents and continuing for several hours thereafter. At 30 minutes post-injection, the three enhancing agents decreased image T1 values as follows:

|  | % Decrease in T1 (30 min post vs. pre) | |
| --- | --- | --- |
|  | liver | kidney |
| Gd:DTPA dimeglumine: | 24.6 | 55.7 |
| Gd:DTPA-dextran microspheres | 54.5 | 26.0 |

Image intensities were increased (enhanced) in inverse proportion to the decreases in T1 relaxation times. The organ pattern of T1 changes (Table above) documented selective liver uptake of Gd:microspheres but not Gd:DTPA dimeglumine (which was concentrated instead, in the kidney). Liver enhancement by Gd:microspheres persisted unchanged for 2.5 hours after Gd:DTPA microspheres but not after Gd:DTPA dimeglumine. (For this latter agent, all liver enhancement was lost after 50 minutes). Thus, optimal selective enhancement of liver was achieved by Gd:DTPA-dextran microspheres at a Gd dose 10–20 times lower than that required for Gd:DTPA dimeglumine agent. These Gd-microspheres also prolonged the interval of image enhancement from minutes to hours. In the post-injection images of animals which received Gd-microspheres (but not Gd:DTPA dimeglumine), the image pixels corresponding to bone marrow were comparably enhanced as assessed by visual inspection, however, the number of pixels corresponding to each rat bone was too small to numerically quantify these changes. Rat spleens could not be imaged due to their small size and proximity to liver, however, in vitro T1 changes of the freshly excised organs indicated that the spleens had enhanced T1's in proportion to those of liver (see next paragraph). Pre-administration T1's were compared to T1's from spleens 35 min after administration of the agents.

T1 and T2 relaxation times of freshly excised organs (read in an IBM PC20 Minispectrometer) decreased in proportion to those obtained from the imager. T1 changes uniformly exceeded the changes in T2 times. In particular, the normalized in vitro T1 changes in rat spleens were:

|  |  | % Decrease in T1 of Spleen (30 min post vs. pre) |
| --- | --- | --- |
| 1. | Gd:DTPA dimeglumine: | 14.4 |
| 2. | Gd:DTPA-dextran microspheres | 61.2 |

Hence, combined in vivo and in vitro analyses indicated that Gd:DTPA-dextran microspheres gave markedly improved enhancement of MR images and/or T1 relaxation in the predicted target organs=liver, bone marrow and spleen.

EXAMPLE 6

IN VIVO NMR IMAGE ENHANCEMENT OF A PRIMARY LIVER TUMOR (HEPATOMA)

Using a direct needle-puncture technique, cell suspensions of the 7777-strain, syngeneic, transplantable, metastasizing Morris hepatoma were injected orthotopically into the right lobes of the livers in 650 gm, Buffalo-strain rats. After two to three weeks the local tumors had reached an average diameter of 0.5 and 1.0 cm. The rats were then imaged both before and after i.v. injections of Gd-DTPA or microsphere Gd-DTPA. MR imaging was performed in a 30cm rf coil with a 0.35 Tesla, Diasonics clinical MRI system (as described above). Post-contrast images were obtained serially beginning immediately after injection and continuing for several hours thereafter.

The Gd:DTPA-dextran microspheres produced a selective enhancement of the tumor (by visual inspection) in relation to surrounding normal liver and all other organs of the rat. Tumor enhancement was maximal in the T1 modes (spin-echo with TR's of 0.5 and 1.0 sec; and inversion recovery) but was also observed in the T2 mode (spin-echo with TR of 2.0 sec). Tumor enhancement became strong at 25 minutes post-injection and persisted unchanged over the 2.5 hour interval of post-injection imaging. Gd:DTPA-dextran microspheres (at 0.011 mmoles/kg) produced image enhancement comparable in intensity to that of Gd:DTPA dimeglumine (at 0.1 mmoles/kg).

The major differences between these two agents were dose (Gd-microspheres gave a more homogeneous enhancement with improved demarcation (contrast) between tumor margins and adjacent normal liver), and persistence of contrast (Gd=DTPA-dimeglumine contrast was significantly reduced by 1.5 hours after injection). In vivo quantification of the increase in tumor image intensity was difficult to obtain because of the small volume of tumor tissue and tumor inhomogeneity. However, in vitro T1 measurement performed on the excised tumor and liver at 2.5 hours corroborated the overall tumor enhancement observed in vivo, as follows:

|  | Buffalo Rat Tissues in Vitro T1 (milliseconds) | |
| --- | --- | --- |
|  | Tumor (hepatoma) | Adjacent normal liver |
| Pre-injection | 782 | 330 |
| Post-injection (2.5 hours) | 530 | 320 |

The percentage decrease in T2 relaxation of tumor tissue post-injection was approximately ⅔ of that observed for T1. The result of enhancement was to brighten the tumor image in relation to surrounding normal liver and other abdominal organs.

EXAMPLE 7

IN VITRO NMR T1 RELAXATION ASSESSMENT OF A NON-LIVER TUMOR (RIF SARCOMA) FOLLOWING IN VIVO INJECTION OF GD:DTPA-DEXTRAN MICROSPHERES

The selective uptake by a primary liver tumor (hepatoma) of Gd-microspheres at the expense of uptake by surrounding normal liver and other body organs was unexpected but reproducible for the 7777 hepatoma line. This fortuitous result was suspected to be atypical for most sold tumors, due to the general absence in such tumors of phagocytic cells responsible for microsphere-Gd uptake. This was further tested by injecting C3H mice in the legs with syngeneic, transplantable RIF sarcomas, allowing the tumors to grow to 1 cm in diameter, and then injecting the mice with Gd:DTPA-dextran microspheres i.v. at a dose comparable to that used above. Pre- and post-injection (45-min) tumors, livers and kidneys were excised and tested in the IBM PC20 Minispectrometer for effects of Gd-microspheres on T1 relaxation times. The results were as shown below.

| Organ/Tissue | T1 of Control (msec) | % Decrease post-injection |
| --- | --- | --- |
| Tumor | 804 | 3.9 |
| Liver | 370 | 20.5 |
| Kidneys | 434 | 7.9 |

Although these latter tumors were in their orthotopic rather than hepatic (liver) locations, the results still suggest strongly that for the usual case of non-primary liver tumors which invade the liver, tumor tissue will, as anticipated, selectively exclude microsphere-Gd, and the surrounding normal liver will relatively concentrate the microsphere agent, leading to enhanced contrast in the reverse pattern from that observed for the preceding hepatoma, namely brighted normal liver surrounded by relatively darker tumor nodules.

Advantages of Gd:DTPA-dextran microspheres as an enhancing agent for liver lesions (and also for spleen and bone marrow lesions) include:

1. Detection of lesions at smaller (potentially millimeter) sizes;
2. Improved demarcation of tumor margins for evaluation of surgical respectability;
3. Prolonged enhancement interval (of hours) for performing serial MR images and shortening the time required for each image;
4. Administration of the lowest dose of Gd (0.007 to 0.024 mmoles/kg) resulting in production of the most minimal toxicity possible with a liver-specific paramagnetic enhancing agent.

EXAMPLE 8

VITRO NMR T1 RELAXATION ASSESSMENT OF A NON-LIVER TUMOR (RIF SARCOMA) FOLLOWING IN VIVO INJECTION OF TWO GD:DTPA-DEXTRAN SOLUBLE POLYMERS

C3H mice, bearing 1 cm transplantable, syngenic RIF sarcomas in their legs (see Examples above), were injected i.v. with two soluble polymeric forms of Gd:DTPA-dextran at a Gd dose of 0.09 mmoles/kg. Tumors, livers and kidneys were excised from pre- and post-injection animals at 60–75 min after injection, and the T1 relaxation times of organs and tumor were determined in the IBM PC20 Minispectrometer for the effects of localized Gd.

| Organ/Tissue | MW of Polymer (/1000) | T1 of Control (msec) | % Decrease post-injection |
| --- | --- | --- | --- |
| 1. Tumor | 70 | 804 | 15.7 |
|  | 10 | " | 3.2 |
| 2. Liver | 70 | 370 | 0.6 |
|  | 10 | " | 7.7 |
| 3. Kidneys | 70 | 434 | 39.7 |
|  | 10 | " | 21.2 |

These results indicate that, as predicted for a nonprimary liver tumor such as RIF, the larger (70,000 MW) soluble polymeric form of Gd:DTPA-dextran gives the reverse pattern of uptake by tumor and liver relative to that just documented for the Gd-microsphere formulation. (This pattern is not seen with the 10,000 MW polymer due to its relatively rapid renal clearance (see above table). If the RIF tumor were Grown in the liver rather than leg of mice, selective uptake of the 70,000 soluble Gd-dextran polymer by intrahepatic RIF tumor would be expected to produce image brightening in the tumor and an unchanged image intensity in the surrounding normal liver (a pattern of enhanced image contrast parallel to that shown above for Gd-microsphere enhancement of liver hepatoma).

EXAMPLE 9

ENHANCED NMR IMAGES OF BLOOD BASED ON CARDIAC DIFFERENTIAL FLOW WITHIN CHAMBERS

Studies were performed indicating that intravenously administered microspheres enhanced T1-weighted blood flow images in the chambers of rat hearts (ungated, 5 minute images), at times up to 20 minutes after injection. Gd:DTPA-dextran microspheres (at 0.3 mmoles Gd/kg) were injected i.v. at time zero into Sprague-Dawley rats and images were obtained immediately and serially each 5 minutes×4 (spin-echo, multi-echo, TR=0.5 and 1.5). Under normal flow conditions, image enhancement was most prominent in the regions of slower flowing blood adjacent to the endocardial surfaces. However, under conditions of generalized slow flow (induced by co-injecting a polycationic polymer at time 0), all portions of the cardiac chambers gave enhanced T-1 weighted blood images.

The soluble Gd:DTPA-dextran polymer, injected at a comparable Gd dose, produced analogous but slightly weaker enhancements. The superior performance of microspheres under flow conditions suggests that factors related to flow turbulence are more effectively overcome by particles that by molecular carriers, and by larger molecules than smaller ones. This interpretation is supported by the finding that the very small MW enhancing agent, Gd-DTPA (dimeglumine) was almost completely ineffective. This ineffectiveness held true even when injections were made directly into the heart and imaged immediately with cardiac gating (R. Peshock, unpublished studies). Hence, it appears that the two new contrast agents are the only ones potent enough to produce noninvasive enhancement of blood flow images with the available methods of clinical MR cardiac imaging.

EXAMPLE 10

TOXICOLOGY

A. Soluble Gd-DTPA-dextran T70

The LD50 in CBA mice of intravenously injected Gd-DTPA-dextran T70 was 12.3 gm/Kg. This was identical to the LD50 of native dextran and resulted from the acute osmotic effects of the dextran carrier. For the preparation used, this total dose corresponded to 2.26 mmol of Gd per Kg. The ratio of toxic/effective dose was 90 (=2.26/0.025 mmol of Gd per Kg). Also, the $LD_{50}$ of Gd-DTPA-dextran T70 was 5 times higher than the $LD_{50}$ of $GdCl_3$. This indicated that there was negligible in vivo release (bioexchange) of chelated Gd.

No significant acute or subacute hepatotoxicity or renal toxicity was observed by histologic assessment after administration of 5 times the effective MRI dose. All mice remained normally active, ate and drank normal quantities of water, and gained weight at the same rate as uninjected litter mates.

B. Microsphere Gd-DTPA-dextran T70

In toxicologic tests, the $LD_{20}$ of Gd-DTPA-dextran microspheres was >1,250 mg/kg. To put this in perspective, image enhancement is carried out at less than 1/5th to 1/11th of the $LD_{20}$ dose, depending on the preparation used. Also, histologic assessment of the major organs excised after MR spectroscopy (in CBA mice) and MR imaging (in Sprague-Dawley and Buffalo rats) revealed no evidence of acute (30-60 min) toxicity.

Preliminary subacute toxicologic studies were performed on CBA mice by injecting them at time 0 with Gd:DTPA-dextran microspheres at a dose (250 mg/kg; 0.06 mmoles/kg Gd) which was approximately 2.5 times the standard dose used for imaging procedures. This was followed by minor elevations (less than or equal to 2 fold) of the liver enzyme, serum glutamic-oxaloacetic transaminase (SGOT) which peaked on day 3-4 at 140% of the values for upper limits of normal and fell back to nearly the control range by day 7 post-injection.

Subacute histologic assessment of the liver (which was assessed by both the Applicant and a specialist in liver pathology) revealed minor zone 1 and 2 changes beginning at 6 hours post injection and comprising slight swelling and vacuolation of hepatocytes. This culminated at day 3-4 in extremely rare single-cell dropout without changes in the quantity or appearance of supporting connective-tissue or portal tracts. These changes largely resolved by day seven. No significant changes in serum creatinine (an indicator of renal function) or renal histology were observed over the 7-day test interval. The mice remained normally active, ate and drank normal quantities of water, and gained weight at approximately the same rate as their uninjected litter mate controls

EXAMPLE 11

PREPARATION AND TESTING OF GLYCEROL-DTPA COPOLYMER

Dried glycerol (0.4 ml, 0.55 Mole) was added to DTPA cyclic dianhydride (296 mg) suspended (by sonification) in 0.4 ml of dried, N,N-dimethylformamide. This mixed suspension was sonicated for an additional 3 min at 20,000 Hz with a special microtip (Heat Systems, Inc.) and heated for 7 hours at 135° C. to give controlled polymerization, plus an additional 2 hours at 155° C. to drive off the reaction solvent (BP=149°-156° C.). The resulting resin was transferred segmentally with sonication into 60 ml of distilled water (pH 5) and sheared for 20 minutes with a high-speed Waring blender. $GdCl_3.7.05H_2O$ (327 mg) was adjusted to pH 5, added dropwise to the DTPA-glycerol resin and again sheared for 3 hours to maximally solubilize the material. The residual larger gel-state material was separated by centrifugation at 250×g for 15 min, and the smaller soluble fraction was saved and separated from residual free Gd by molecular filtration (with 4 washes of distilled water, pH 5.0) through a 1000 MW cutoff filter under pressurized nitrogen. The retentate was saved and centrifuged for an additional 15 min at 1000×g and the supernatant of this was saved and lyophilized 16 hours.

Although initially it had the appearance of a gel, the resulting glycerol-DTPA:Gd copolymer was minimally to negligibly cross-linked as determined by molecular filtration, which gave a size range (for 95% of the material) of 1,000 to 10,000 MW, with an estimated average of 2,200 MW. This confirmed that the copolymeric units were soluble but that they had a tendency, as formulated presently, to undergo ionic inter molecular aggregation at a high concentration, which was reversible at a low concentration.

In vitro testing for T1 relaxation effects in the IBM PC20 Minispectrometer gave the following result (compare, for example the table of Example 3):

| | Dose Decreasing T1 by 50% | |
|---|---|---|
| | total wt (ug/ml) | Gd (M/10$^{-5}$) |
| Gd:DTPA-glycerol copolymer | 32 | 5.0 |

Thus, on the basis of Gd molarity, Gd:DTPA-glycerol copolymer was 1.9 times as active as Gd:DTPA dimeglumine. Its R1 was greater than 100/(mM and sec).

In vivo tests were carried out by injecting CBA mice i.v. with 130 mg/kg of Gd:DTPA-glycerol copolymer and determining the effects of T1 relaxation times of organs freshly excised at 30 minutes after agent administration.

| | Control T1 (msec) | Injected T1 (msec) | % Decrease |
|---|---|---|---|
| Liver | 339 | 200 | 41.0 |
| Kidney | 343 | 223 | 35.0 |

Thus, as presently formulated, Gd:DTPA-glycerol copolymer was considerably more active as a MR enhancing agent for liver than was Gd:DTPA dimeglumine on both a weight and Gd molar basis. (It is expected that this effect should be overcome by formulations which decrease intermolecular aggregation by altering electrostatic charge or pH; or by adding inert, chain-separating molecules. Preliminary acute toxicologic studies were very slightly inferior to those of the Gd:DTPA-dextran soluble polymer. It is anticipated that this toxicity should be improved by substituting the hexadentate chelator, TTHA, for DTPA. This would leave 4 carboxylic acid groups available for Gd chelation (as with DTPA-dextran), and hence, theoretically decrease Gd bioexchange in vivo.

EXAMPLE 12

CONJUGATION OF BINDING GROUPS TO THE GD:DTPA-DEXTRAN POLYMERS AND MICROSPHERES

Approximately 50 mg of the dextran-DTPA polymer or 150 mg of particles were suspended in 9.5 ml distilled water with 0.05M NaCl. Sodium periodate (0.05M, 300 ul) was added and the mixture stirred at 22° C. for 30 min. The preparation was washed with distilled water (by molecular filtration, polymer; or centrifugation, microspheres) and brought up in 15 ml distilled water or saline. To the periodate-oxidized preparation were added the materials to be covalently conjugated: antibody, avidin, or biotin hydrazide, at 1–3 mg each, depending on the number of reactive groups on the additive. This mixture was stirred again for 30 minutes, then $NaBH_4$ (8 mg) was added to reduce the Schiff base (or its equivalent) and stirring was continued for an additional 15 min. The pH was adjusted to 7.5, and the stabilized preparation was washed and resuspended in 1 ml of 0.02M phosphate-buffered in 0.15M NaCl containing 0.25% dextran T70. Microspheres derivatized by this method had between 2500 and 5000 available binding sites per 0.5 urn sphere, as assessed by the high-stability specific binding of $^{125}I$-avidin to biotinylated microspheres prepared with biotin hydrazide.

This method allows the direct covalent conjugation of antibodies and other receptor binding proteins or peptides via their reactive amino groups; and the indirect coupling of (a) biotinylated antibodies (commercially available) to avidin-derivatized polymer or spheres; or (b) native antibodies to polymer or spheres pre-derivatized with Protein A (Pharmacia Chemicals) which binds the Fc region of antibodies at high affinities

EXAMPLE 13

PREPARATION AND TESTING OF ALBUMIN MICROSPHERES CONTAINING THE ENTRAPPED, NONCOVALENTLY BOUND METAL ION-CHELATE COMPLEX, GADOLINIUM DIETHYLENETRIAMINE PENTAACETIC ACID (Gd:DTPA)

A 0.95M solution of Gd:DTPA in dimeglumine (2×N-methylglucamine) salt form (Schering AG, Germany/Berlex Laboratories, Inc., USA) was added at 0.25 ml to a maximally concentrated solution of human serum albumin (125 mg, Sigma Chemical Co.) in distilled water (0.25 ml). This was stirred for 20 minutes, added dropwise to 30 ml of cottonseed oil (Sargent Welch Scientific), and sheared for 20 minutes with a high-speed Waring-type blender to produce submicron droplets (0.1–0.6 um diameter). This emulsion was added dropwise to a preheated (140° C.) rapidly stirring, 100-ml volume of cottonseed oil, in order to heat denature (stabilize) the albumin matrix and maintain the integrity of particles and entrapment of Gd:DTPA upon subsequent suspension in injection medium. Heating at 140° C. was continued for 10 min with high-speed shearing. The emulsion was cooled to 220° C. with continued mixing. Oil was extracted with 6×60 ml of fresh diethyl ether (containing antioxidant) (Fisher Scientific Co.), and the resulting microspheres were lyophilized for 16 hrs to remove residual ether. Particles ranged from 0.1–0.5 um (diameter) with a mean of 0.3 urn (monitored by light and electron microscopy).

Microspheres (Gd:DTPA:dimeglumine:albumin) were tested in vitro using a 20 MHz pulsed Nuclear Magnetic Resonance (NMR) spectrometer, for their capacity to reduce the T1 relaxation time of water protons in physiologic saline solution (0.02M phosphate-buffered, 0.15M NaCl). Activity was expressed as the concentration of material required to decease the T1 relaxation time to 50% of the value for phosphate-buffered saline ($ID_{50}$). Microspheres were suspended at a concentration of 1 mg/ml by brief sonification. Because albumin microspheres have a fast-release (surface) component of Gd:DTPA as well as a controlled-release (interior) component, the spheres were washed, resuspended, and diluted serially for testing.

| Material | $ID_{50}$ (total weight) |
|---|---|
| Unwashed microsphere suspension | 0.25 mg/ml |
| Fast-release supernatant | 0.30 mg/ml |
| Washed microspheres | 3.8 mg/ml |
| Gd:DTPA dimeglumine | 0.084 mg/ml |

Microspheres (Gd:DTPA:dimeglumine:albumin) were tested in vivo by injecting them intravenously into 25 gm CBA mice (2 animals per group), allowing 30 minutes for uptake and sequestration by liver Kupffer cells, sacrificing the mice, and testing the excised organs. The acute (30-min) biodistribution was determined by injecting microspheres trace-labeled with $^{125}I$-albumin. Radioisotope was quantified in a standard gamma counter.

| Organ | $^{125}I$ counts: % of total recovered at 30 min | $^{125}I$ counts: per gm of target organ |
|---|---|---|
| Blood | 7.2 | 10.8 |
| Spleen | 0.8 | 32.8 |
| Liver | 57.6 | 119.0 |
| Lungs | 31.5 | 369.1 |
| Kidneys | 2.9 | 26.2 |
| Total | 100.0 | |

The pattern of uptake by liver and spleen (with moderate acute lung sequestration) is typical of that for small (<3 um) particles.

The T1-weighted proton relaxation times of mouse livers were quantified by determining the whole-organ T1 relaxation time in a 20 MHz NMR spectrometer.

| Injected material | Liver T1 (msec) | % of Control |
|---|---|---|
| Saline (0.15 M) | 332 | Control |
| Albumin microspheres (45 mg/kg, total wt; 0.1 mmol/kg Gd) | 314 | 94.5 |
| Gd:DTPA dimeglumine (0.1 mmol/kg Gd) | 327 | 98.5 |

At equivalent doses (normalized to in vitro T1 potency), the formulation of Gd:DTPA:dimeglumine albumin microspheres was slightly more potent than soluble Gd:DTPA dimeglumine. The high dose of albumin carrier needed to achieve this modest T1-relaxation, makes albumin a suboptimal matrix material for delivering Gd to the liver for applications specifically involving magnetic resonance imaging and specstroscopy. This high dose was necessitated by the marked sequestration of Gd in the interior of microspheres and the very slow release (½ in 8 hrs) of Gd:DTPA from spheres which are sufficiently stabilized to give effective liver targeting.

EXAMPLE 14

PREPARATION OF Gd:DTPA:DIETHYLAMINOETHYL DEXTRAN SOLUBLE POLYMER AND Gd:DTPA:DIETHYLAMINOETHYL MICROSPHERES CONTAINING NONCOVALENTLY BOUND Gd:DTPA (WITH STRONG ION PAIRING BETWEEN DTPA AND THE DEAE SUBSTITUENTS OF DEXTRAN); AND UNLOADED DTPA:DIETHYLAMINOETHYL-DEXTRAN MICROSPHERES (WITHOUT CHELATED Gd)

Solution 1. Diethylenetriamine pentaacetic acid, 0.72 gms (DTPA, SIgma Chemical Co.) was dissolved in 2.5 ml distilled water, the pH adjusted to 7.2 with NaOH, mixed with $GdCl_3.6H^2O$, 0.34 gms, and the solution readjusted to pH 7.2 and stirred for 20 min to allow complete chelation of Gd. Solution 2. Diethylaminoethyl dextran (DEAE dextran, 500,000 MW with 1 positively charged group per 3 glucose residues, Sigma Chemical Co.) was dissolved by warming a saturated solution of 1 gm in 2.5 ml of distilled water. To prepare the soluble polymeric form of Gd:DTPA:DEAE-dextran, Solutions 1 and 2 were mixed with vigorous stirring; the pH was adjusted to 7.2 and the mixture washed twice with distilled water (20 ml per wash) to remove unbound Gd. The soluble polymer was concentrated to 50-100 mg/ml by molecular filtration under pressurized nitrogen through a 100,000 MW cutoff filter (Amicon Corporation, XM100). To prepare the microsphere form of Gd:DTPA:DEAE-dextran, DEAE dextran was stirred vigorously into 30 ml of cottonseed oil (Sargent Welch Scientific) until an even emulsion was produced. To this was added 1 ml (dropwise) of Solution 1. This emulsion was sonicated for 6 min. (with continuous magnetic stirring) using a 20,000 Hz ultrasonifier with a 3 mm special microtip (Heat Systems, Inc.) to disrupt the aqueous phase into 0.2-0.4 um microdroplets. Microparticles were stabilized and water removed by heating to 120° C. for 20 min with vigorous stirring. After cooling, oil was removed with 3×60 ml of fresh diethyl ether (containing antioxidant) (Fisher Scientific Co.), and the sample lyophilized for 16 hrs. Microspheres ranged from 0.1 to 0.3 um, with a mean diameter of 0.2 um.

Unloaded DTPA:DEAE-dextran microspheres. An alternative microsphere formulation was prepared without chelated Gd (or other metal ions), by dissolving DTPA, adjusting the pH to 7.2, and mixing this with a 1-gm solution of DEAE dextran, all prepared as described above. The aqueous phase was emulsified in cottonseed oil and processed as described above.

EXAMPLE 15

LOADING (CHELATION) BY DTPA:DEAE-DEXTRAN MICROSPHERES OF THE PARAMAGNETIC METAL IONS, $Gd^{+3}$ AND $Fe^{+3}$ a. Chelation of $Gd^{+3}$. DTPA:DEAE-dextran microspheres, 100 mg, from Example 13, were added to 280 mg of $GdCl_3.6H_2O$ dissolved in 2 ml of distilled water and stirred for 30 min. Unbound gadolinium was removed by washing twice with 20 ml of distilled water (pH 5.5) using a 300,000 cutoff, 43mm diameter filter (Amicon Corporation, XM300) under pressurized nitrogen. The microspheres were removed from the filter with 2 ml of distilled water and lyophilized to dryness (16 hrs). microspheres ranged from 0.1 to 0.5 um (diameter).

b. Chelation of e . DTPA: DEAE-dextran F +3 microspheres, 100 mg, from Example 14, were added to 350 mg of $FeCl_3.6H_2O$ and processed as in Example 15.a. (above) to remove unbound $Fe^{+3}$. Particles ranged from 0.15 to 0.6 um in diameter.

EXAMPLE 16

IN VITRO TESTING OF SOLUBLE Gd:DTPA POLYMERS AND Gd:DTPA MICROSPHERES PREPARED IN EXAMPLES 14 AND 15

Test materials were diluted serially and assayed for proton T1 relaxivities using a 20 MHz pulsed NMR spectrometer as described in Example 3. These materials contained very minor components of fast-released Gd and Gd:DTPA chelate (less than 2% of the totals). Thus, it was not necessary to wash and resuspend the materials prior to NMR testing. The ID50 concentrations were:

| Material | $ID_{50}$ (total weight) |
| --- | --- |
| Gd:DTPA:DEAE-dextran soluble polymer | 0.125 mg/ml* |
| Gd:DTPA:DEAE-dextran microspheres | 0.160 mg/ml |
| DTPA:DEAE-dextran microspheres, loaded subsequently with Gd | 0.175 mg/ml |
| Gd:DTPA dimeglumine | 0.084 mg/ml* |

*Molar concentrations of Gd = 4.6 × 10 − 5 M for the Gd:DTPA:DEAE-dextran soluble polymer and 9.0 × 10 − 5 M for Gd:DTPA dimeglumine.

The soluble Gd:DTPA:DEAE-dextran polymer was 1.96 times more potent than Gd:DTPA dimeglumine. This improved relaxivity was attributable to strong nonvocalent binding of the negatively charged, DTPA moiety of Gd:DTPA to the positively charged, DEAE substituent groups of dextran polymer. The large size of this polymer (300,00 MW) resulted in a longer rotational correlation time for each noncovalently bound Gd:DTPA and allowed improved transfer of energy from water protons to paramagnetic Gd ions.

EXAMPLE 17

IN VITRO HISTOLOGIC STAINING OF Fe:DTPA MICROSPHERES AS PREPARED IN EXAMPLE 15

Fe:DTPA:DEAE-dextran microspheres were suspended at 1 mg/ml in a 70% ethanol-water solution, 10-50 uL aliquots were placed on cytologic glass slides, the microspheres were sedimented at 750×g for 12 min. in a cytocentrifuge, slides were air dried, and microsphere:$Fe^{+3}$ was stained for histologic analysis by the Prussian blue, acidic ferro-ferricyanide procedure. Dark blue reaction product formed over each microsphere, as assessed by standard light microscopy. Hence, the chelated $Fe^{+3}$, which was initially bound to microsphere DTPA at neutral pH, became dissociated sufficiently by the acidic pH of the staining solution to allow histochemical detection in vitro.

EXAMPLE 18

IN VIVO TESTING OF SOLUBLE Gd:DTPA POLYMERS AND Gd:DTPA MICROSPHERES PREPARED IN EXAMPLES 15 AND 16 a. Proton T1 Relaxation Times in Mouse Organs

Test materials were injected i.v. into 25 gm CBA mice. At 30 min the mice were sacrificed by decapitation (exsanguination) and the excised livers and kidneys assessed for changes in proton T1 relaxation times (20 MHz; IR pulse sequence). Doses of test materials were made equivalent based on in vitro potency ($ID_{50}$ analysis).

| Material | Dose (mmol/kg) | T1 (% of control)* Liver | T1 (% of control)* Kidney |
|---|---|---|---|
| Gd:DTPA:DEAE dextran soluble polymer | 0.23 | 81 | 78 |
| Gd:DTPA:DEAE dextran microspheres | 0.23 | 81 | 78 |
| Gd:DTPA dimeglumine | 0.47 | 83 | 24 |

*The T1's of control organs were 330 msec for liver and 385 msec for kidney.

The soluble polymeric formulation of Gd:DTPA:-DEAE dextran was the most potent substance for liver (approximately 4 times as potent as Gd:DTPA dimeglumine, which produced a significantly greater decrease in kidney). The microsphere form of Gd:DTPA:DEAE dextran was approximately 2 times as potent in liver as Gd:DTPA dimeglumine. Because of selective organ uptake by the liver, it produced a much smaller effect in kidney. Gd:DTPA dimeglumine was relatively ineffective at decreasing the T1 of liver even at very high doses which produced marked decreases in kidney. (The usual dose of the dimeglumine formulation used for Phase III clinical trials is 0.1 mmol/kg.)

b. Proton Magnetic Resonance Imaging and Correlation With the Proton T1 Relaxation Times in Rats Test materials were injected intravenously into 500 gm Sprague-Dawley rats. At approximately 30 minutes, the rats were placed in the head coil of a 0.35 Tesla clinical imaging device (Diasonics Corp.), and T1-weighted images (using both a spin-echo pulse sequence at TR's of 0.5, 1.5 and 2.0, and an inversion recovery sequence) were obtained on image slices of 0.5 cm thickness taken through the liver and kidneys. T1 relaxation times were determined from the TR=0.5 and 2.0 data using area-averaging of signal intensities and a proprietary software program for calculations. At the completion of imaging, the rats were sacrificed by decapitation (exsanguination). Their livers, kidneys and spleens were excised, tested for in vitro correlations with the in vivo changes in proton T1 relaxation times and then placed in buffered formalin fixative for histopathologic evaluation.

The doses of test materials were as follows:

| | Gd (mmol/kg) |
|---|---|
| Gd:DTPA:DEAE dextran soluble polymer | 0.30 |
| Gd:DTPA:DEAE dextran microspheres | 0.15 |
| Gd:DTPA dimeglumine | 0.30 |

| Test Material | Organ | T1 (% of control) In vivo | T1 (% of control) In vitro* |
|---|---|---|---|
| soluble polymer | liver | 65 | 64 |
| | spleen | NT** | 48 |
| | kidney | 77 | 8 |
| microspheres | liver | 63 | 53 |
| | spleen | NT | 43 |
| | kidney | 63 | 23 |
| dimeglumine | liver | 83 | 88 |
| | spleen | NT | 86 |
| | kidney | 57 | 25 |

*Control proton T1 values were: liver, 275 msec; spleen, 464 msec; kidneys, 492 msec.

**Not tested. Splenic images could not be obtained in the rat due to very small organ size and anatomic juxtaposition tot he liver.

There was a direct correlation between in vivo and in vitro T1 relaxation times for liver. For kidney, the correlations were sporadic due to difficulties in (a) determining average image intensities on these much smaller organs, and (b) obtaining sharp demarcation between the differently enhancing anatomic subregions of kidney (cortex and medulla). Image intensities increased in inverse proportion to changes in T1. Soluble polymeric Gd and microsphere Gd gave preferential image enhancement of liver relative to kidney, as compared to the reciprocal changes obtained for Gd:DTPA dimeglumine. After normalizing for dose and image intensity, microsphere Gd was 5 times more potent for liver enhancement than Gd:DTPA dimeglumine, and soluble polymeric Gd was 2.5 times more potent. Bone marrow was also preferentially enhanced by the soluble polymeric and microsphere Gd. These changes were noted visually but could not be quantified due to the small number of image pixels corresponding to the bones of rats.

EXAMPLE 19

HISTOLOGIC ASSESSMENT OF THE SELECTIVE UPTAKE BY LIVER AND SPLEEN OF MICROSPHERES CONTAINING THE PARAMAGNETIC METAL ION, $Fe^{+3}$ $Fe^{+3}$:DTPA:DEAE-dextran microspheres (prepared as in Example 14) were injected into a CBA mouse at a dose of 140 mg/kg. Thirty minutes after injection, the animal was sacrificed, and the liver and spleen were excised. The tissues were fixed in formalin and stained using the Prussion blue (acidic ferro-ferricyanide) iron staining technique, to identify cellular locations of microsphere iron. By microscopic evaluation, 0.1–0.6 tun (diameter) heavy concentrations (3+/4+) of iron-positive particles were present in Kupffer cells of the liver and sinusoidal macrophages of the spleen. Other parenchymal cells of the liver (hepatocytes) and spleen were negative for iron staining, as were other organs (bone marrow was not tested). These results indicate that the $Fe^{+3}$:DTPA chelate was bound (noncovalently) to the DEAE dextran with a sufficient affinity to survive in vivo transit through the bloodstream and become cleared acutely as intact particle-associated iron by the phagocytic cells of liver and spleen. This histologic result documents that the preferential MR enhancement of liver images and the preferential T1 changes of splenic water proton relaxation times (above) were caused by the selective uptake of paramagnetically labeled particles by phagocytic cells in the "target" organs.

EXAMPLE 20

ACUTE TOXICOLOGIC ASSESSMENT OF Gd:DTPA:DEAE DEXTRAN SOLUBLE POLYMER AND THE Gd:DTPA:DEAE DEXTRAN MICROSPHERES OF EXAMPLE 14

The rats of Example 17 which were injected with soluble polymeric and microsphere Gd noncovalently bound (ion) paired) to DEAE dextran, developed mild-to-moderate respiratory distress between 90 and 120 minutes after the injection of test materials. Based on these observations, histologic evaluation was performed on the formalin-fixed organs (brain, heart, lungs, liver, spleen and kidneys) from these rats and from CBA-strain mice injected with the same material at identical doses. The lungs, liver and kidneys of both the rats and mice revealed slight-to-moderate acute congestion of the small blood vessels with red blood cells). Additionally, the kidneys showed moderate acute cortical edema (accumulation of protein-poor fluid). These histologic changes documented an acute toxic effect of the two DEAE dextran-based formulations of Gd. The histologic changes in CBA mice were uniformly more pronounced than those in the Sprague-Dawley rats used for magnetic resonance imaging. These inter-species differences make it uncertain if similar effects would occur in humans. The nature of the major histologic change, acute congestion, strongly suggested that the multiple, positively charged DEAE groups of the dextran matrix, had probably interacted with the negatively charged surfaces of cells which line the blood vessel walls (endothelial cells) and had induced endothelial changes that led to red cell adherence and accumulation. From the standpoint of interpreting the image enhancement and T1 changes of Example 14, it is important that the histologic changes just described did not occur at the time when the images were performed (30 minutes following injection of test materials) but rather, at 90 to 120 minutes following injection. Hence, taken together, Examples 16 and 18 establish the efficacy (but not the biological compatibility) of Gd:DTPA noncovalently bound to polycationic carriers, as prototype formulations for preferential MR image enhancement of liver, spleen and bone marrow.

EXAMPLE 21

PREPARATION OF HEPARIN-STABILIZED Gd:DTPA DIMEGLUMINE MICROSPHERES

A 0.95M solution of Gd:DTPA dimeglumine (Schering Ag-Berlex) was concentrated by nitrogen evaporation, adjusted to pH 10, added at 1.8 ml to 100 ml of cottonseed oil, and homogenized for 15 min with a Waring high-speed blender to produce fine microdroplets (0.2–0.5 um). This emulsion was stabilized at 130° C. for 20 min with continued shearing. Heparin, 5000 units (Upjohn Co. clinical grade from beef lung) was added to neutralize the net positive charge of the outer surfaces of these particles and to confer additional particle stability upon subsequent resuspension. The positive surface charge of particles (which had been found in Example 19 to produce acute vascular toxicity) was conferred (in the present example) by the amine moieties of N-methylglucamine (dimeglumine). The reason for coating particle surfaces with heparin was to neutralize this positive charge and eliminate the related acute toxicity. The oil was extracted with diethyl ether and the particles lyophilized as in Example 12. Resulting microspheres were 0.1–0.4 um in diameter. The in vitro NMR proton T1 activity was:

| Material | $ID_{50}$ |
| --- | --- |
| Gd:DTPA:dimeglumine: heparin microspheres | 0.045 mg/ml |
| Gd:DTPA:dimeglumine | 0.084 mg/ml |

Based on the molar concentration of Gd, the microsphere formulation was approximately twice as active as the soluble one.

EXAMPLE 22

IN VIVO TESTING OF HEPARIN-COATED Gd: DTPA: DIMEGLUMINE MICROSPHERES

Microspheres were injected intravenously into CBA mice at a dose calculated to deliver 0.19 mmol of Gd/kg. The percentage decreases in proton T1 relaxations of the experimental versus control (uninjected) organs excised at 30 minutes were:

Liver: 6%
Kidney: 53%

Hence these microspheres were not sufficiently stabilized to remain intact long enough for clearance by the liver and spleen (requiring approximately 15 minutes). The addition of supplementary matrix materials such as 70,000 MW dextran, would be expected to confer this required stability.

Histologic assessment of acute vascular toxicity was performed in CBA mice as described in Example 20. No congestion nor edema were observed.

Based on the preceding examples of polymer and microsphere efficacy, stability, and toxicity, the preferred embodiments were covalently conjugated dextran-DTPA polymers and microspheres in conjunction with chelated Gd.

EXAMPLE 23

IN VITRO T1 EFFECTS OF $Fe^{+3}$ CHELATED TO DTPA-DEXTRAN SOLUBLE POLYMER $FeCl_3.6H_2O$ was added in a stoichiometric quantity to DTPA-Dextran T10 (11,000 MW soluble polymer) and the T1 $ID_{50}$'s compared with those of comparably loaded Fe:DTPA and Fe:desferrioxamine (a low molecular weight iron chelator of bacterial origin.

| Substance | T1 ($ID_{50}$) Fe($M/10^{-5}$) |
| --- | --- |
| Fe:DTPA-dextran 11,000 MW soluble polymer | 18 |
| Fe:desferrioxamine | 113 |
| Fe:DTPA | 37 |

Fe:DTPA-dextran polymer was the most potent of 3 agents tested by a multiple of 2 over Fe:DTPA

EXAMPLE 24

In Vivo Imaging of a Human BRO Melanoma (Grown in Nude Mice) With Soluble Gd-dextran T70

These studies are performed using the rapidly proliferating, amelanotic, BRO human melanoma grown to a weight of 2.0–6.0 gms in the axillary soft tissues of Swiss-strain nude mice. The amelanotic nature of the tumor avoids any potential for alteration of unenhanced tissue-relaxation times by naturally occurring paramagnetic substances which have been described for pigmented melanomas. The axillary location of tumors allows imaging of the tumor and liver in adjacent slices. This shortens the imaging time for each group of mice and provides maximal anatomic separation of tumors from the higher-intensity kidneys and bladder. MR imaging is performed on a Diasonics 0.35T instrument, using a 30-cm rf coil, and a T1-weighted spin-echo pulse sequence (TR 500, TE 40). Pentobarbital is used for animal anesthesia in order to avoid drug modulation of image intensities. T1 relaxation were performed on the freshly excised organs. In general, these T1's decreased in proportion to increased image intensities. Deviations from this relationship were observed for enhancement with Gd:DTPA dimeglumine if the interval between peak image contrast and sacrifice of the animals became unusually prolonged. The potencies of Gd-DTPA-dextran T70 and Gd-DTPA (dimeglumine) were compared by injecting both agents at the limiting dose for Gd:DTPA dimeglumine of 0.03 mmols Gd per kg. Under these limiting conditions, enhancement of the BRO melanoma occurred prominently with Gd:DTPA-dextran T70 but was barely perceptible with Gd:DTPA dimeglumine which required a dose ½ log higher. Image contrast was maintained for a significantly longer post-injection interval by Gd:DTPA*dextran T70 than Gd:DTPA dimeglumine. The new soluble polymeric agent had the following advantages:

1. Improved Gd potency in vivo (by a factor of ≧3.3);
2. Improved contrast gradient between tumor and surrounding normal tissues, which improves the detection of body tumors;
3. Improved discrimination of internal tumor structures;
4. Presence of an early "vascular phase" of tumor enhancement, which may improve the detection of small and infiltrating tumors at their most rapidly growing borders;
5. Prolongation of tumor contrast.

EXAMPLE 25

ALTERNATIVE CHEMICAL MEANS FOR CONJUGATION OF CHELATING SUBSTANCES TO CARRIER POLYMERS

In certain instances chemical advantages, such as increased stability of metal ion chelation or increased flexibility of the carrier polymer, may be achieved by using conjugation reactions other than direct derivatization with dicyclic DTPA anhydride. For example, the middle acetate group of DTPA may be selectively reacted with ethylene diamine before decylizing the stronger-chelating carboxylic anhydrides. This may be accomplished by conjugation in dried organic solvents such as N,N-dimethyl-formamide or N,N-diethylacetamide using standard organic-soluble carbodiimide techniques.

The amine-derivatized DTPA could then be reacted in aqueous solvents, using water-soluble carbodiimide reagents, with the OH groups of native dextran, the aldehyde groups of sodium periodate-oxidized dextran (more reactive), or the carboxylic acid groups of succinylated dextran (most reactive) which had been prepared by prior reaction with succinic anhydride. Alternatively the simple DTPA chelate could be stabilized in its most favored chelation state by prebinding Gd, followed by conjugation to ethylene diamine in aqueous solvents using water-soluble carbodiimide. Such metal-protection techniques are common methods for protecting enzyme active sites during enzyme chemical reactions/purifications. The resulting dextran conjugate might have even higher binding stability for Gd and other paramagnetic metals than does the completely acceptable conjugate described as the preferred embodiment in the present application.

Additional alternative methods for potentially improved or diversified conjugation includes (1) modified acid-catalyzed di-anhydride-alcohol reactions (W. C. Eckelman, et al., J. Pharm. Sci. (1975), 643:704); (2) amide coupling linkages between ethylenediamine derivatized DTPA and succinylated dextran as modified from (D. J. Hnatowich et al., J. Nuc. Med. (1981) 22:810) or direct coupling techniques involving penta-triethylammonium DTPA, isobutylchloroformate and triethylamine hydrochloride precipitation to form the reactive species, carboxycarbonic anhydride of DTPA, which may be used for various alternative conjugations (G. E. Krejcarek and K. L. Tucker, Biochem. Biophys. Res. Comm. (1977), 77:581). These reactions are expected to expand and potentially improve the already satisfactory techniques of the present application.

In the above-described studies, radionuclide quantification of Gd binding to the DTPA-dextran soluble polymer was performed using $^{153}$Gd, in collaboration with Padmaker Kulkarni, Ph.D. (Radiology, Imaging Center, University of Texas Health Science Center, Dallas, (UTHSCD); and magnetic resonance imaging was performed on the University's Diasonics 0.35T clinical magent in a 30-cm rf head coil using T1-weighted, spin-echo and inversion-recovery pulse sequences, in collaboration with Jeffrey Weinreb, M.D., William Erdman, M.D., and Jesse Cohen, M.D., Nuclear Magnetic Resonance Imaging Center-Radiology, University of Texas Health Sciences Center, Dallas, Tex.

Changes may be made in the construction, operation and arrangement of the various parts, elements, steps and procedures described herein without departing from the concept and scope of the invention as defined in the following claims.

I claim:

1. An image-enhancing agent or spectral enhancing agent comprising:
   a biodegradable, water-soluble polysaccharide or oligosaccharide carrier-material comprising repeating hydrophilic monomeric units having amino, quaternary ammonium, sulfate, carboxyl or hydroxyl groups; and
   a chelating agent comprising functional groups bound noncovalently by strong ionic interaction to an amino, quaternary ammonium, sulfate, hydroxyl or carboxyl group of the monomeric units, said chelating agent having a formation constant for divalent or trivalent metal cations at physiological temperature and pH, of at least about $10^8$; and
   a paramagnetic metal ion bound to the chelating agent, usable to enhance internal images or spectra, arising from induced magnetic resonance signals;
   wherein the image-enhancing agent has a molecular diameter of less than about 3 nanometers, contains less than about 5% (w/w) cross-linked or microaggregated species and is biodegradable by hydrolytic or other enzymatic or physiologic mechanisms of animals or intestinal microorganisms, to intermediary metabolites, excretable chelates, polymers, oligomers, monomers or combinations thereof, all of low toxicity.

2. The image-enhancing agent of claim 1 wherein the chelating agent is DTPA.

3. The image-enhancing agent of claim 1 wherein the carrier-material has a molecular weight between about 1,000 daltons and about 500,000 daltons.

4. The image-enhancing agent of claim 1 wherein the carrier-material is dextran.

5. The image-enhancing agent of claim 1 wherein the carrier-material has a molecular weight between about 40,000 daltons and about 75,000 daltons.

6. The image-enhancing agent of claim 1 wherein the functional groups are carboxyl groups.

7. The image-enhancing agent of claim 1 in which the functional groups are non-covalently bound to the carrier-material by a quaternary ammonium group covalently conjugated to the carrier-material.

8. The image-enhancing agent of claim 1 in which the functional groups are non-covalently bound to the carrier-material by a sulfate group which is covalently conjugated to the carrier-material.

9. The image-enhancing agent of claim 6 wherein the chelating agent is DTPA.

10. The image-enhancing agent of claim 7 wherein the chelating agent is DTPA.

11. The image-enhancing agent of claim 8 wherein the chelating agent is DTPA.

12. The image-enhancing agent of claim 1 wherein the paramagnetic metal ion is selected from the group of elements having atomic numbers 21–29 and 57–70.

13. The image-enhancing agent of claim 1 wherein the paramagnetic metal ion is that of gadolinium, iron, nickel, copper, erbium, europium dysprosium, holmium, chromium or manganese.

14. The image-enhancing agent of claim 1 wherein the chelating agent is in a molar ratio of chelating agent/monomeric unit between about 1/5 and about 1/25.

15. The image-enhancing agent of claim 1 wherein the paramagnetic metal ion is that of gadolinium.

16. The image-enhancing agent of claim 1 wherein the chelating agent is DTPA and the paramagnetic metal ion is that of gadolinium.

17. The image-enhancing agent of claim 1 wherein the carrier-material is dextran, the paramagnetic metal ion is that of gadolinium and the chelating agent is DTPA.

18. The image-enhancing agent of claim 1 wherein the water-soluble carrier-material comprises heparin, heparan sulfate, chondroitin sulfate, dermatan sulfate, starch, carboxymethylstarch or hydroxyethylstarch individually, in combinations with each other or with DEAE dextran.

19. The image-enhancing agent of claim 18 wherein the water soluble carrier-material comprises heparin and DEAE dextran.

20. The image-enhancing agent of claim 18 wherein the chelating agent is DTPA.

21. The image-enhancing agent of claim 18 defined further as comprising gadolinium.

22. The image-enhancing agent of claim 18 wherein the water soluble carrier-material comprises DEAE-dextran and heparin and the image-enhancing agent further comprises DTPA bound to the DEAE dextran by ion-pair bonding.

23. The image-enhancing agent of claim 1 wherein the water soluble carrier-material is heparin.

24. The image-enhancing agent or spectral enhancing agent useful with external or internal magnetic resonance imaging or spectroscopy, the agent comprising a biodegradable polysaccharide or oligosaccharide carrier-material; a DTPA chelating agent non-covalently bound by strong ionic interactions to said carrier material; and a paramagnetic metal ion bound to said chelating agent.

25. The image-enhancing agent of claim 24 wherein the paramagnetic metal ion is gadolinium.

26. The image-enhancing agent of claim 25 in which the agent is in a completely water soluble form having a molecular diameter less than about 3 nanometers and is useful for imaging of:
   internal tumors, at a potency multiple of at least about 3.3 times that of Gd-DTPA when administered by an intravenous route; and
   body cavities and gastrointestinal tract upon direct introduction, with the exception of the stomach, due to dechelation of gadolinium at pH's of about 1 to 3.5.

27. The image-enhancing agent of claim 25 in which the agent is in a completely water soluble form of less than about 3 nanometers in molecular diameter, and clears rapidly from the blood and body, primarily by a renal route, with at least about 80% of an injected gadolinium dose clearing from the body within less than about 6 hours of injection.

28. The image-enhancing agent of claim 24 wherein the agent is in a completely water-soluble form having a molecular diameter of less than about 3 nanometers and an osmotic activity of less than about 50 mOsm per kg of agent and also less than about 28 mOsm per micromole of gadolinium.

* * * * *

UNITED STATES PATENT AND TRADEMARK OFFICE
CERTIFICATE OF CORRECTION

PATENT NO.   :   5,336,762

DATED        :   August 9, 1994

INVENTOR(S)  :   David F. Ranney

It is certified that error appears in the above-identified patent and that said Letters Patent is hereby corrected as shown below:

In claim 24, column 40, line 17, delete the term "The" and insert the term --An-- therefor.

In claim 28, column 40, line 45, immediately after the numeral '24' insert the term --or 25--.

Signed and Sealed this

Twenty-eight Day of February, 1995

Attest:

BRUCE LEHMAN

*Attesting Officer*       *Commissioner of Patents and Trademarks*